(12) United States Patent
Burrell

(10) Patent No.: US 6,468,799 B1
(45) Date of Patent: Oct. 22, 2002

(54) GENETICALLY MODIFIED PLANTS WITH ALTERED STARCH

(75) Inventor: Michael Meyrick Burrell, Cambridge (GB)

(73) Assignee: Advanced Technologies (Cambridge) Limited, London (GB)

( * ) Notice: Subject to any disclaimer, the term of this patent is extended or adjusted under 35 U.S.C. 154(b) by 0 days.

(21) Appl. No.: 09/444,728

(22) Filed: Nov. 18, 1999

(30) Foreign Application Priority Data

Nov. 19, 1998 (GB) .............................................. 9825242

(51) Int. Cl.$^7$ ............................. C12N 15/29; C12N 5/04

(52) U.S. Cl. ...................... 435/468; 435/69.1; 536/102; 536/23.6; 536/24.1

(58) Field of Search ................................ 536/102, 23.6, 536/24.1; 435/468, 69.1

(56) References Cited

U.S. PATENT DOCUMENTS

| | | | | |
|---|---|---|---|---|
| 5,648,111 A | * | 7/1997 | Pearlstein et al. | 426/578 |
| 5,969,214 A | * | 10/1999 | Stalker et al. | 800/205 |
| 6,255,114 B1 | * | 7/2001 | Lightner et al. | 435/468 |

FOREIGN PATENT DOCUMENTS

| | | | |
|---|---|---|---|
| WO | WO 92/11362 | * | 7/1992 |
| WO | WO 92/11376 | | 7/1992 |
| WO | WO 92/11382 | | 7/1992 |
| WO | WO 94/09144 | * | 4/1994 |
| WO | WO 94/11520 | | 5/1994 |

OTHER PUBLICATIONS

U.S. patent application Ser. No. 09/521,972, filed Mar. 9, 2000, Burrell et al.

Baecker et al., 1983, "Biosynthesis of bacterial glycogen. Primary structure of *Escherichia coli* 1,4-α-D-glucan:1,4-α-D-glucan 6-α-D-(1,4-α-D-glucano)-transferase as deduced from the nucleotide sequence of the glgC gene", J. Biol. Chem. 258:5084-5088.

Bartels and Thompson, 1986, "Synthesis of mRNAs coding for abundant endosperm proteins during wheat grain development", Plant Sci. 46:117-125.

Bradford, 1976, "A rapid and sensitive method for the quantitation of microgram quantities of protein utilizing the principle of protein–dye binding", Anal. Biochem. 72:248-254.

Cheng et al., 1997, "Genetic transformation of wheat mediated by *Agrobacterium tumefaciens*", Plant Physiol. 115:971-980.

Clackson and Winter, 1989, ""Sticky–feet"–directed mutagenesis and its application to swapping antibody domains", Nucl. Acids Res. 17:10163-10170.

Echt and Schwartz, 1981, "Evidence for inclusion of controlling elements within the structural gene at the waxy locus in maize", Genetics 99:275-284.

(List continued on next page.)

Primary Examiner—Ralph Gitomer
Assistant Examiner—Devesh Khare
(74) Attorney, Agent, or Firm—Pennie & Edmonds LLP

(57) ABSTRACT

Starch of wheat and maize plants is altered by the introduction of a chimeric gene comprising a glycogen synthase coding sequence under the control of a promoter directing expression and a terminator. A transit peptide for translocation of the glycogen synthase to the plant plastid may also be included in the chimeric gene. The starch has altered processing characteristics, in particular an increased chain length.

15 Claims, 14 Drawing Sheets

OTHER PUBLICATIONS

Edwards et al., 1999, "A combined reduction in activity of starch synthases II and III of potato has novel effects on the starch of tubers", Plant J. 17:251–261.

Fromm et al., 1990, "Inheritance and expression of chimeric genes in the progeny of transgenic maize plants", Bio/Technology 8:833–839.

Gordon–Kamm et al., 1990, "Transformation of maize cells and regeneration of fertile transgenic plants", Plant Cell 2:603–618.

Guerineau et al., 1988, "An expression cassette for targeting foreign proteins into chloroplasts", Nucl. Acids Res. 16:11380.

Keeling, 1997, "Plant biotechnology: technical barriers to starch improvement", Starch: Structure and Functionality 180–195, Eds. Frazier et al., Royal Society of Chemistry, Cambridge, UK.

Kiel et al., 1994, "Glycogen in *Bacillus subtilis*: molecular characterization of an operon encoding enzymes involved in glycogen biosynthesis and degradation", Mol. Microbiol. 11:203–218.

Kortstee et al., 1997, "Characterization of starch from genetically modified potato after transformation with the bacterial branching enzyme of *anacystis nidulans*", in: Starch: Structure and Functionality, Frazier et al., eds., Royal Society of Chemistry, Cambridge, UK, pp. 238–247.

Kuipers et al., 1994, "Formation and deposition of amylose in the potato tuber starch granule are affected by the reduction of granule–bound starch synthase gene expression", Plant Cell 6:43–52.

Kumar et al., 1986, "Biosynthesis of bacterial glycogen. Primary structure of *Escherichia coli* ADP–glucose:$\alpha$–1,4–glucan,4–glucoseyltransferase as deduced from the nucleotide sequence of the glgA gene", J. Biol. Chem. 261:16256–16259.

Le Bail et al., 1997, "Structural and polymorphic transitions of amylose induced by water and temperature changes", in:*Starch: Structure and Functionality*, Frazier et al., eds., Royal Society of Chemistry, Cambridge, UK, pp. 51–58.

Leung and Preiss, 1987, "Cloning of the ADPglucose pyrophosphorylase (glgC) with glycogen synthase (glgA) structural genes from *Salmonella typhimurium* LT2", J. Bacteriol. 169:4349–4354.

Raleigh et al., 1989, Current Protocols in Molecular Biology, Ausubel et al., eds., Wiley Interscience, New York, Unit 1.4.

Schägger and von Jagow, 1987, "Tricine–sodium dodecyl sulfate–polyacrylamide gel electrophoresis for the separation of proteins in the range from 1–100 kDa", Anal. Biochem. 166:368–379.

Shewmaker et al., 1994, "Expression of *Escherichia coli* glycogen synthase in the tubers of transgenic potatoes (*Solanum tuberosum*) results in a highly branched starch", Plant Physiol. 104:1159–1166.

Tester, 1997, "Starch: the polysaccharide fractions", in: *Starch: Structure and Functionality*, Frazier et al., eds., Royal Society of Chemistry, Cambridge, UK, pp. 163–171.

Uttaro and Ugalde, 1994, "A chromosomal cluster of genes encoding ADP–glucose synthetase, glycogen synthase and phosphoglucomutase in *Agrobacterium tumefaciens*", Gene 150:117–122.

Vasil et al., 1992, "Herbicide–resistant fertile transgenic wheat plants obtained by microprojectile bombardment of regenerable embryogenic callus", Bio/Technology 10:667–674.

Visser et al., 1991, "Expression of a chimaeric granule-–bound starch synthase–GUS gene in transgenic potato plants", Plant Mol. Biol.17:691–699.

Visser et al., 1991, "Inhibition of the expression of the gene for granule–bound starch synthase in potato by antisense constructs", Mol. Gen. Genet. 225:289–296.

* cited by examiner

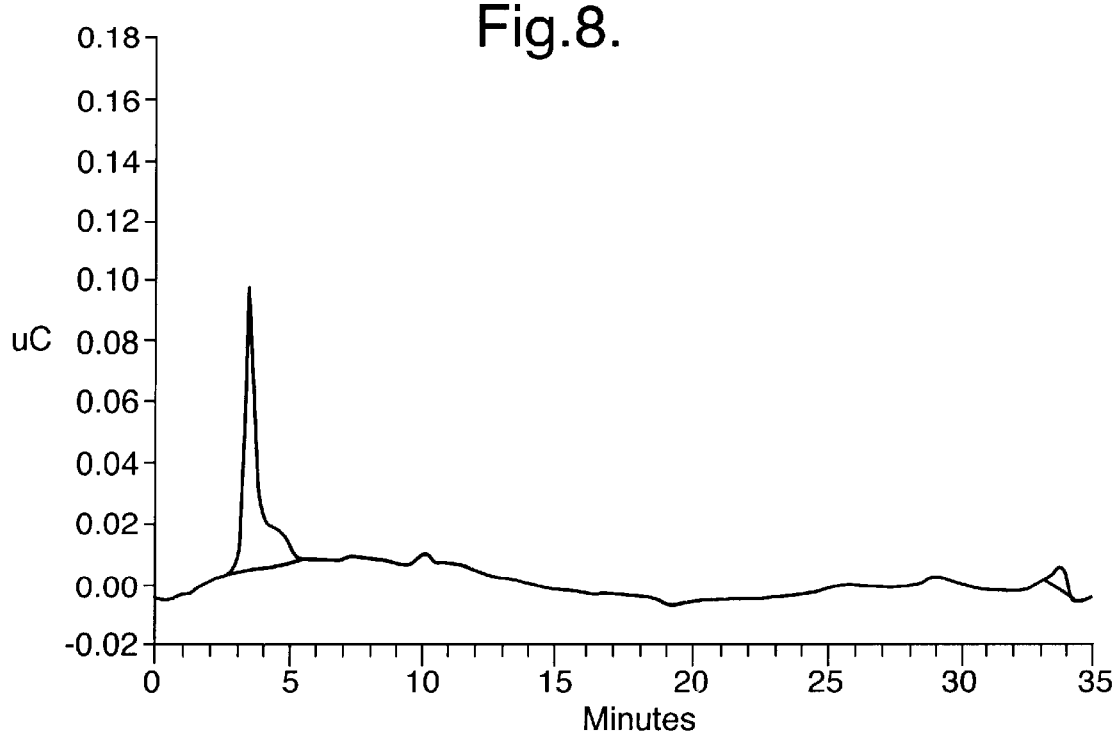
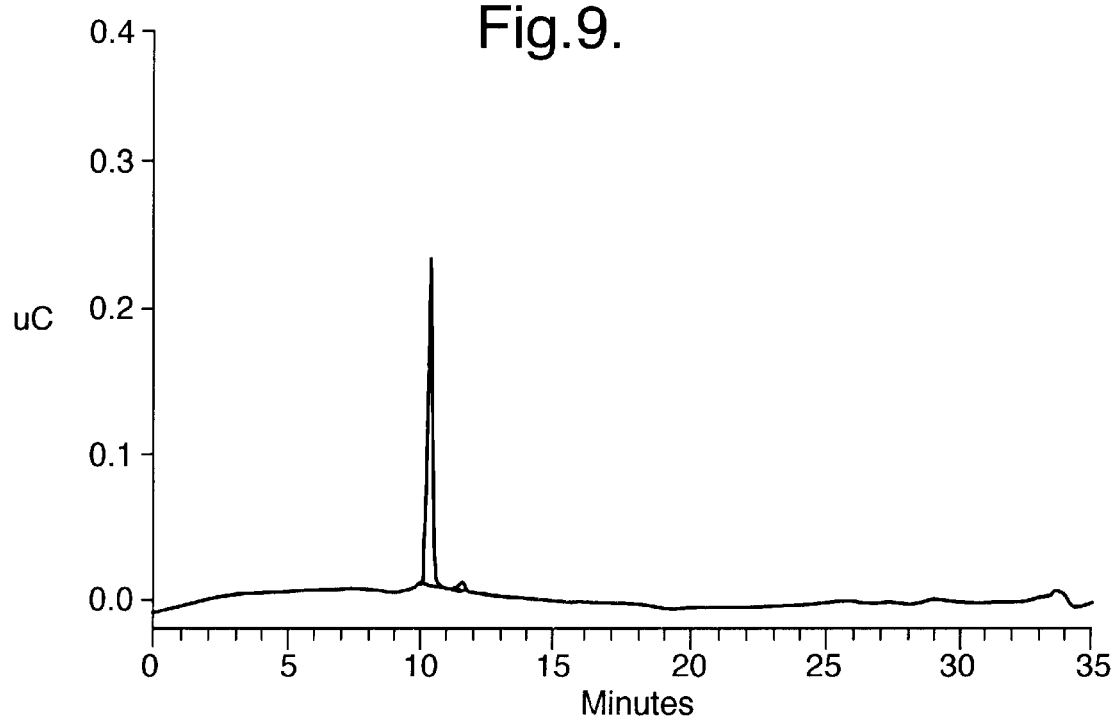

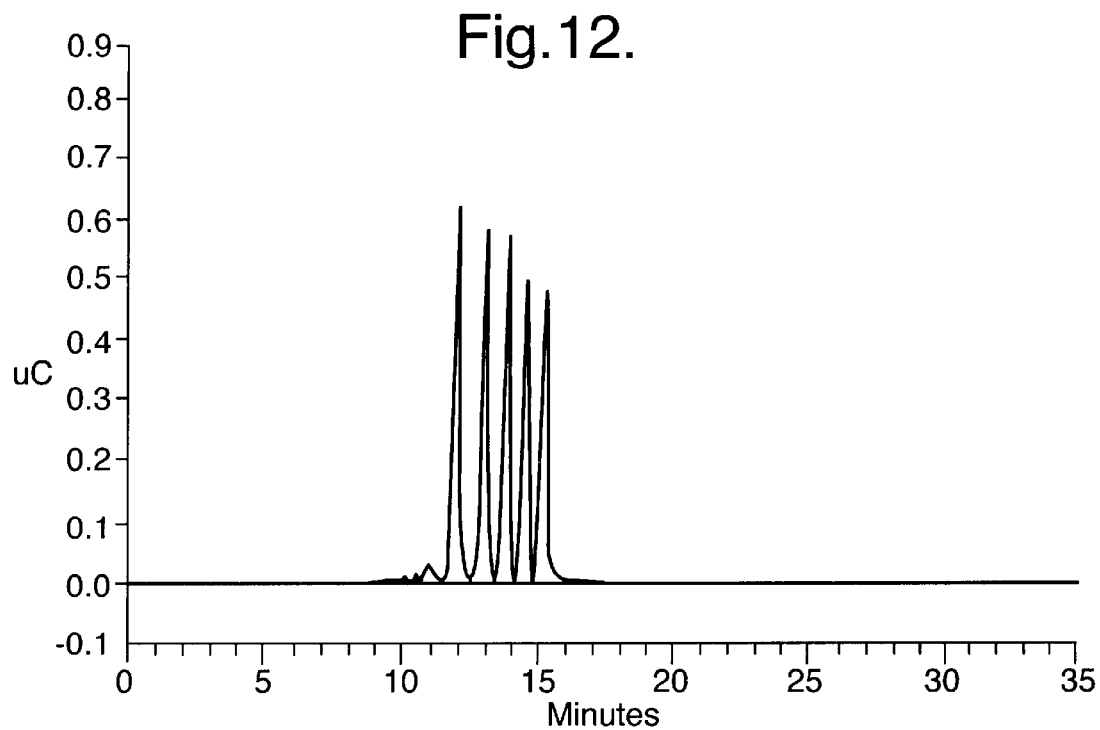
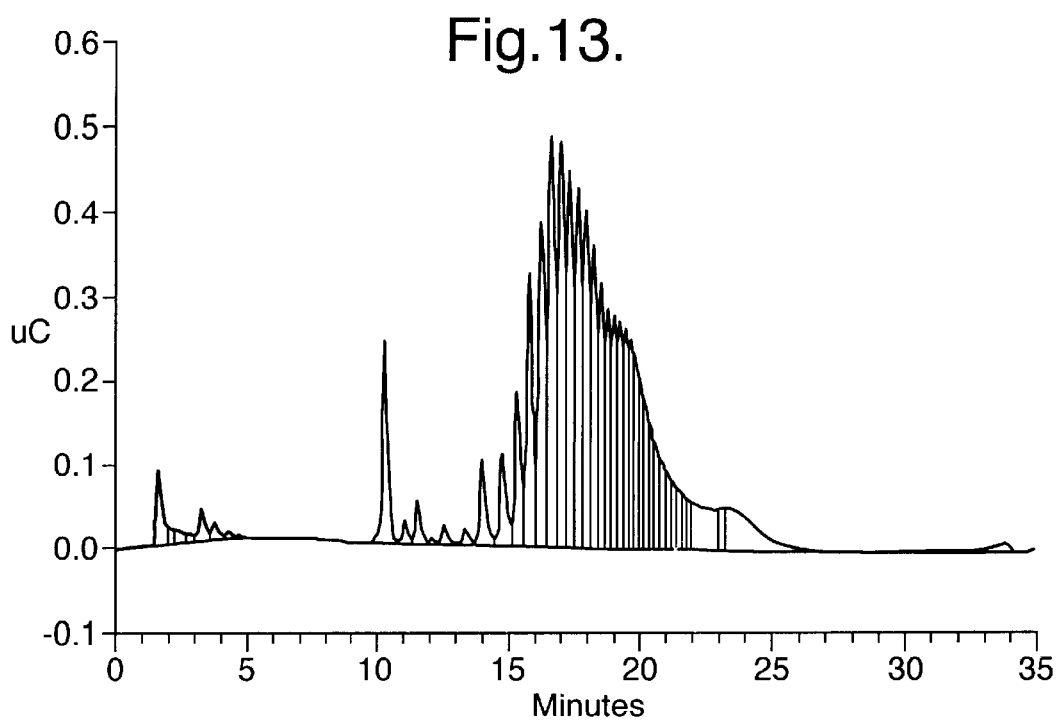

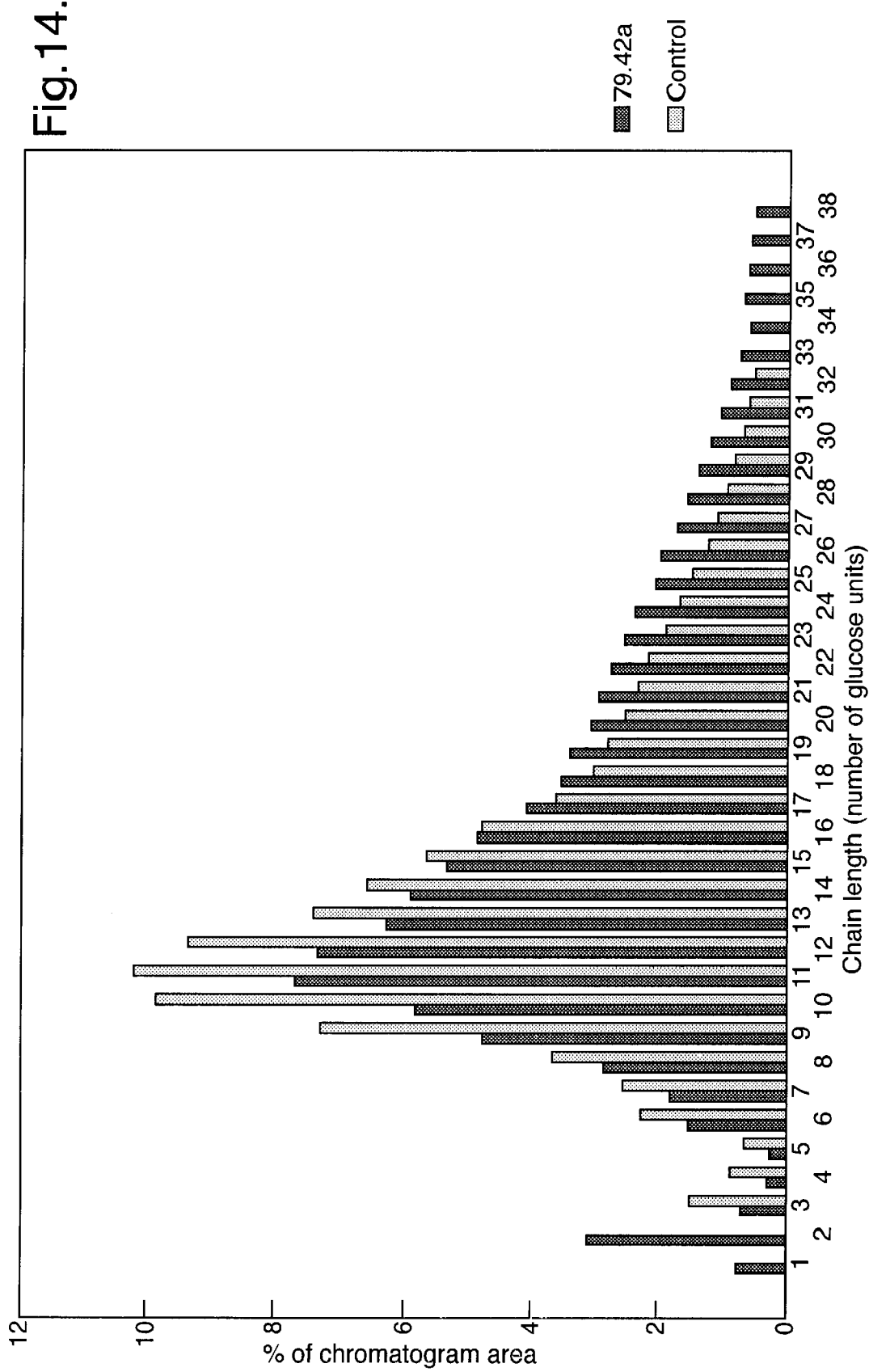

US 6,468,799 B1

GENETICALLY MODIFIED PLANTS WITH ALTERED STARCH

1. INTRODUCTION

This invention relates to genetically modified plants, and in particular to genetically modified maize and wheat. The genetically modified plants have an altered starch synthesizing ability following the introduction, by recombinant DNA techniques, of one or more gene sequences coding for enzymes in the starch or glycogen biosynthetic pathway into the plant.

2. BACKGROUND OF THE INVENTION

Starch is a complex polymer of glucosyl residues. It is the major form in which carbohydrate is stored in the tissues and cells of most species of higher plants. It is accumulated in the leaves of plants during the day as a result of photosynthesis and is used to supply the needs of the plant for energy and biosynthesis during the night. Starch is also accumulated in non-photosynthetic cells, especially those involved in reproduction such as in seeds, fruits and tubers. Therefore, starch is of great importance to the productivity of the plant and its survival.

Starch is also highly significant to man. Firstly, it forms a major component of animal diets, supplying man and his domestic animals with a large portion of their carbohydrate intake. Secondly, the type of starch in a plant affects the quality of the processed plant product. Thirdly, starch is used industrially in the production of paper, textiles, plastics and adhesives, as well as providing the raw material for some bioreactors. Starch from different species have preferred uses. On a world scale, starch producing crops are agriculturally and economically by far the most important, and these crops include wheat, maize, rice and potatoes. The type of starch will affect the quality of a processed product and the profitability of the processed crop. In addition, the quantity and quality of starch present in the harvested organ of a plant will affect the gross yield and the processing efficiency.

In plants, i e., vascular plants, the starch consists of linear chain and branched chain glucans known as amylose and amylopectin respectively. Starch with various amounts of amylose and amylopectin are found in different plants. Typically, plant starch contains 10–25% amylose, the remainder being amylopectin, the branched chain glucan. Amylopectin contains short chains and long chains, the short chains ranging from 5–30 glucose units and the long chains ranging from 30–100 glucose units, or more. It is thought that the ratio of amylose to amylopectin and the distribution of short to long chains in the amylopectin fraction affect the physical properties of starch, e.g., thermal stabilization, retrogradation and viscosity. These properties also affect the utility of starch, as mentioned above. Starches from different plants have different properties, which also affects their suitability for processing under certain conditions and for certain uses. It can be seen, therefore, that modifying the starch generated in a plant can have particular utility in the downstream processing or the yield of the starch in the plant storage organ.

For example, waxy corn starch lacks amylose and this starch has unique properties. Also, most mutations in the waxy locus of maize, which encodes starch granule bound synthase I (GBSSI), result in plants which produce much reduced amylose. When no functioning GBSSI is synthesized in the homozygous waxy mutant, it also lacks amylose (Echt & Schwartz, 1981).

The genetic modifications of the present invention produce altered starch composition and properties, which properties are ideally beneficial in terms of starch processing.

3. SUMMARY OF THE INVENTION

This invention seeks to transform cereal crops and specifically wheat and maize with an enzyme involved in the synthesis of microbial glycogen, namely glycogen synthase (E.C.2.4.1.21).

This invention also seeks to modify properties of the starch in these transformed plants which are particularly useful and/or advantageous in the downstream processing of starch or the plant itself.

The present invention provides transgenic wheat or maize plants, said plants having therein a chimeric gene comprising a promoter, operably associated with a coding sequence for glycogen synthase, and a terminator. The genetically modified plants have an altered starch synthesizing ability following the introduction, by recombinant DNA techniques, of a coding sequence for glycogen synthase.

In another embodiment, more than one gene sequences coding for enzymes in the starch or glycogen biosynthetic pathway may be introduced into the plant in addition to the coding enzyme for glycogen synthase.

The present invention provides a method of altering the starch in maize or wheat plants, the method comprising the steps of stably introducing into the plant genome a nucleic acid sequence encoding glycogen synthase under the direction of a suitable promoter and a suitable terminator, and regenerating a plant having an altered genome.

The present invention also provides novel forms of starch which can be obtained from said transgenic cereal crop plants, e.g., transformed wheat or maize, and which is characterized by an altered chain length and/or modified processing properties as compared to starch prepared from a non-transgenic cereal crop plant. A composition comprising the altered starch obtained from the transgenic plants is contemplated. Preferably, the altered starch is purified.

Plant cells containing a chimeric gene comprising a nucleic acid sequence encoding glycogen synthase are also an aspect of this invention, as are other plant parts, such as for example, seed of the transformed plant containing a chimeric gene according to the invention.

4. DESCRIPTION OF THE FIGURES

In order that the invention may be easily understood and readily carried into effect, reference will now be had, by way of example, to the following diagrammatic drawings in which:

FIG. 8 shows a standard chromatogram of glucose at 1 mM concentration;

FIG. 9 shows a standard chromatogram of maltose at 1 mM concentration;

FIG. 12 shows a standard chromatogram of a mixture of maltotriose, maltotetraose, maltopentaose, maltohexaose and maltoheptaose each at 1 mM concentration;

FIG. 13 shows a chromatogram of an isoamylase digest of wheat starch from wheat plants according to the invention;

FIG. 14 shows a graph of starch branch chain lengths for starch from the seed of a single transgenic wheat plant compared with starch from the seed of a control wheat plant;

Figure 17:
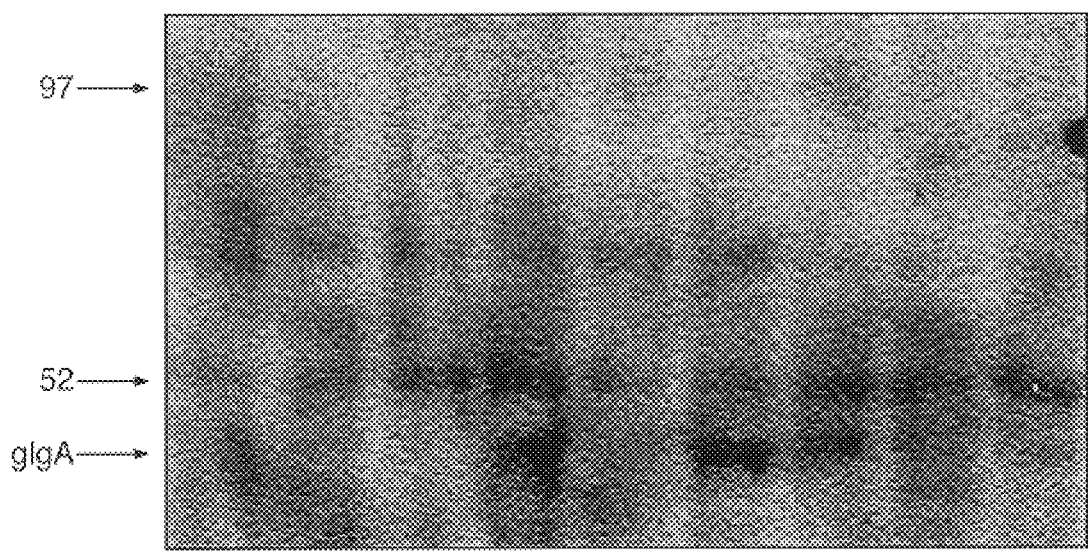

FIG. 17 shows a western blot of proteins extracted from the seed of transgenic maize plants according to the invention. 1 (A-F) refers to the proteins extracted from different seeds of the maize plant 2 AM4–5'-2; and 2 (A-B) refers to proteins extracted from the seeds of the maize plant 2-AM4–6'-1. -ve is a non transgenic control.

5. DETAILED DESCRIPTION OF THE INVENTION

This invention relates to genetically modified plants. The genetically modified plants have an altered starch synthesizing ability following the introduction, by recombinant DNA techniques, of one or more gene sequences coding for enzymes in the starch or glycogen biosynthetic pathway into the plant.

In the last few years this concept of modifying starch properties has been postulated but never put into practice in cereal plants, such as maize and wheat. The patent literature International Patent Application, Publication No. WO 94/11520 (Zeneca) described constructs having a target gene which encodes an enzyme involved in the starch or glycogen biosynthetic pathway under control of a gene switch, for example, a chemical or temperature controlled on-off mechanism. Various crops were postulated as being suitable for use in the method but no plant transformation was actually carried out. Some constructs were made but no examples or results were given. International Patent Application, Publication No. WO 94/09144 (Zeneca) was very similar to the just described application. Only the first steps in the transformation process were demonstrated. No results are given for any plant, and only the transformation of tomato is described with reference to the exemplary methodology, although other plants are mentioned. International Patent Application, Publication No. WO 92/11376 (Amylogene) described introducing antisense genes for GBSSI in to potatoes to down-regulate amylose production with the intention of producing a potato with practically no amylose-type starch. Whilst great detail is given of methodology, no actual results from transformed plants are given and no plant transformations other than potato are postulated. Only a small number of constructs are actually produced to enable one to carry out the invention. The results for potato were eventually published in the scientific literature by Visser et al., in 1991. Increases in the amylopectin content of the starch was seen. Further scientific papers on altering GBSSI in potato using antisense GBSSI constructs, e.g., Visser et al., (1991a) and Kuipers et al., (1994), have shown actual transformation and alteration of starch composition.

In terms of successful transformation using non-plant derived starch-related genes, in International Patent Application, Publication No. WO 92/11382 (Calgene) and their later publication (Shewmaker et al., 1994) potato was actually transformed with E. coli glgA (Glycogen synthase) and E. coli glgC (ADPG pyrophosphorylase). Higher specific gravity measurements were obtained from transformed potato plants compared with two control events, as well as altered starch characteristics.

It can be seen, therefore, that work to date has involved introducing certain genes involved in glycogen biosynthesis specifically into potato. The effects and their potential usefulness for other plants and other non-plant derived starch-related genes has only been postulated.

The turnover of starch in leaves is of central importance to the growth of the plant. A change in the structure of the starch in the granule without a complementary change in other enzymes of starch breakdown might be expected to restrict the export of carbon from the leaf at night. This might be expected to cause an altered ratio of source to sink with a subsequent effect on yield.

The present invention provides a method of altering the starch in maize or wheat plants, the method comprising the steps of stably introducing into the plant genome a nucleic acid sequence encoding glycogen synthase under the direction of a suitable promoter and a suitable terminator, and regenerating a plant having an altered genome.

The present invention also provides novel forms of starch which can be obtained from said transgenic cereal crop plants, e.g., transformed wheat or maize, and which is characterized by an altered chain length and/or modified processing properties as compared to starch prepared from a non-transgenic cereal crop plant. In a preferred embodiment, the invention provides a composition comprising starch purified from said transgenic cereal crop plants. Methods for preparing a composition comprising starch and for purifying starch from various parts of a cereal plant are well known in the art.

The modified starch provided by the invention preferably has an altered chain length and/or processing property compared with control starch from a non-transformed plant. Other characteristics of the starch that are expected to be modified, and that can be assessed by methods known in the art include but are not limited to the degree of retrogradation, viscosity, pasting temperature, and gelling temperature (Edwards, et al., 1999; Frazier, et al., 1997). The modified starch of the invention may also have altered properties with respect to chemical derivitization.

As used herein, the term 'operably associated' refers to an association in which the regulatory regions (e.g., promoter, enhancer) and the nucleic acid sequence to be expressed are covalently joined and positioned in such a way as to permit transcription, and under the appropriate condition, translation.

As used herein, the term chimeric gene refers to a combination of nucleic acid sequences for each part of the chimeric gene, which sequences have been engineered into relationship by recombinant DNA techniques, which sequences may also be in their separate parts endogenous or exogenous to the plant into which the chimeric gene is to be introduced.

Moreover a variant of glycogen synthase can also be used in the present invention. A variant may comprise one or more changes in the amino acid sequence of the enzyme, e.g., by way of addition, substitution, or deletion of one or more amino acids, compared with the wild type enzyme. Any change should not abolish the ability of the enzyme to perform its function, though it may increase or decrease this ability depending on the nature of the changes. Preferably, the amino acid changes are conservative.

In various embodiments, the glycogen synthase, fragment, variant analog, or derivative may be expressed as a fusion, or chimeric protein product (comprising the enzyme, fragment, analog, or derivative joined via a peptide bond to a heterologous protein sequence (of a different protein)). Such a chimeric gene product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Preferably, the fragment, analog, and derivative of the enzyme in the fusion protein retains the ability to perform the enzyme's function.

The present invention also provides novel forms of starch which can be obtained from said transgenic cereal crop plants, e.g., transformed wheat or maize, and which is characterized by an altered chain length and/or modified processing properties as compared to starch prepared from a non-transgenic cereal crop plant.

Preferably the promoter is capable of directing expression in a particular issue of the plant and/or at particular stages of development of the plant. The promoter may be heterologous or homologous to the plant. Preferably the promoter directs expression to the endosperm of the plant seed. A preferred promoter is the high molecular weight glutenin (HMWG) gene of wheat Other suitable promoters will be known to the skilled man, such as the promoters of gliadin, branching enzyme, ADPG pyrophosphorylase, starch synthase and actin, for example.

Preferably the chimeric gene also contains a sequence that encodes a transit peptide which provides for translocation of the glycogen synthase and/or a marker gene or other coding sequence to the plant plastid. Suitable transit peptides include those from the small sub-unit of the ribulose bisphosphate carboxylase enzyme (ssu of Rubisco) from pea, maize or sunflower, for example. Combinations of transit peptides may also be used. Other suitable transit peptides for transporting to the amyloplast will be known to those skilled in the art, such as the transit peptide for the plant plastid acyl carrier protein (ACP) or for GBSSI.

The coding sequence encoding glycogen synthase is advantageously a sequence obtained from a microorganism, such as a unicellular organism, algae or bacteria, or alternatively from a mammalian source, which sequence has the necessary ability to encode glycogen synthase.

Suitably the glycogen synthase is derived from a bacterial source such as *E. coli* (for example, Baecker, P. A. et al., 1983 or Kumar, A. et al., 1986), Agrobacterium (Uttaro, A. D., & Ugalde, R. A. 1994), Salmonella (Leung, P. S. C. & Preiss, J. 1987), or Bacillus (Kiel, J. A. et al., 1994). Standard methods of cloning by hybridization or polymerase chain reaction (PCR) techniques may be used to isolate the sequences from such organisms: for example, molecular cloning techniques such as those described by Sambrook, J. et al., 1989 and the PCR techniques described by Innis, M. A., et al., 1990. Nucleic acid molecule in other organisms encoding a glycogen branching enzyme can also be obtained by a similar method.

Depending on the homology of the nucleotide sequences encoding glycogen synthase enzymes, different conditions of stringencies may be used in the hybridization procedures. By way of example and not limitation, hybridization procedures using such conditions of high stringency are as follows: hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) .Other conditions of high stringency which may be used are well known in the art. Hybridization procedures using conditions of moderate stringency that may be used are as follows: hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (Ausubel et al., 1989, supra). Other conditions of moderate stringency which may be used are well-known in the art.

The chimeric gene may comprise one or more additional coding sequences from the starch or glycogen biosynthetic pathway, such as, for example, branching enzyme (E.C. 2.4.1.18).

The transformation techniques for the method of the invention are advantageously direct DNA transfer techniques, such as electroporation, microinjection or DNA bombardment (the biolistic approach). Alternatively, plant cell transformation using plant vectors introduced into plant pathogenic bacteria, such as Agrobacterium-mediated transfer (Cheng, M. et al. (1997)), may be used. In both methods selectable markers may be used, at least initially, in order to determine whether transformation has actually occurred. Useful selectable markers include enzymes which confer resistance to an antibiotic, such as gentamycin, hygromycin, kanamycin and the like. Alternatively, markers which provide a compound identifiable by a color change, such as GUS, or luminescence, such as luciferase, may be used.

The chimeric gene may also comprise a gene switch mechanism which determines under what conditions or when the coding sequence is to be expressed. The gene switch may be a chemically induced promoter or a temperature controlled promoters for example.

6. EXAMPLES

The invention will now be described, by way of example, with reference to an embodiment for incorporating glgA from *E. coil* strain LCB618 into wheat and maize.

6.1 Materoa;s amd Abbreviations

LB—Luria broth
TF—Tris-HCl, 1 mM EDTA
SDS—sodium dodecyl sulphate
CTAB—cetyltrimethyl ammonium bromide
dATP—2'-deoxy adenosine 5' triphosphate
dTTP—2'-deoxy thymidine 5' triphosphate
dCTP—2'-deoxy cytosine 5' triphosphate
dGTP—2'-deoxy guanosine 5' triphosphate
DTT—dithiothreitol
ATP—adenosine 5' triphosphate
HEPES—N-[2-hydroxyethyl]piperazine-N-[2-ethanesulfonic acid]
NBT—nitroblue tetrazolium BCIP—5-bromo-4-chloro-3-indolyl phosphate
GST—glutathione S transferase
NAD—nicotinamide adenine dinucleotide
IgG—immunoglobulin G Example 1: Construction of glgA Plasmids Used for Particle Bombardment of Wheat Embryos 6.1.1. Isolation of E. coli Chromosomal DNA The coding sequence for glgA was originally isolated by PCR using chromosomal DNA from the *E. coli* strain LCB618 as template. *E. coli* LCB618 was obtained from *E. coli* Genetic Stock Center. Yale University, U.S.A.

*E. coli* LCB618 was grown up in 100 ml LB o/n at 37° C. Cells were pelleted and re-suspended in 9.5 ml 10 mM Tris-HCl, 1 mM EDTA (TE) pH 8.0 and 0.5 ml 10% w/v Sodium dodecyl sulphate (SDS) and 50 ul proteinase K 20 mg/ml were added. The mixture was incubated at 37° C. for 1 hour to lyse cells. 1.8 ml of 5 M NaCl followed by 1.5 ml of CTAB (cetyl trimethyl ammonium bromide)/NaCl solution (10% w/v CTAB in 0.7 M NaCl) were added and the mixture incubated at 65° C. for 20 minutes. The lysate was extracted with an equal volume of chloroform and centrifuged at 6,000 g to separate the layers. The upper layer was removed to a fresh tube and DNA was precipitated by the addition of 0.6 volumes isopropanol. The DNA was removed from the solution with a sealed pasteur pipette, placed into a fresh tube and washed with 70% ethanol. The DNA was dried in vacuc and resuspended in TE pH 8.0. The DNA was purified on a CsCl gradient.

6.1.2. Sticky-feet PCR

In order for the *E. coli* glycogen synthase to function in plants the protein has to be transported into the amyloplast. This transport can be facilitated by attachment of a plastid transit peptide to the amino terminus of the *E. coli* polypeptide.

The coding sequence for the transit peptide (TP) from the small subunit of the ribulose bisphosphate carboxylase enzyme (ssu of Rubisco) pea has been cloned and the TP shown to target β-glucuronidase (GUS) protein to chloroplasts (Guerineau et al., 1988).

Figure 1:
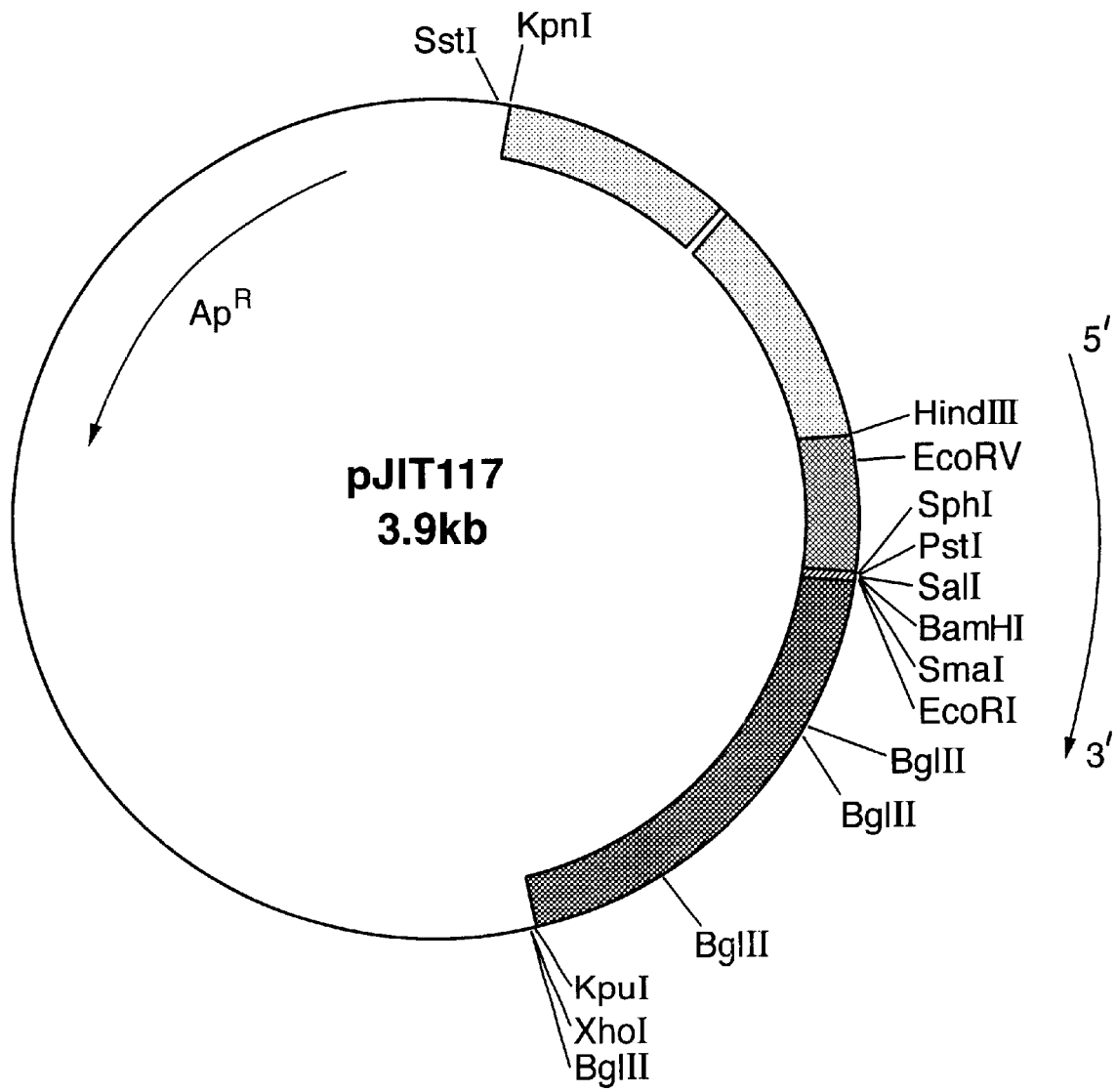
FIG. 1 shows a map of the plasmid pJIT117 used in the preparation of the plasmid of FIG. 2.

The plasmid pJIT117 (Guerineau et al., 1988), the map of which is shown in FIG. 1, has several restriction sites downstream of the ssuTP which can be used for subcloning of coding sequences, however, the subcloning must create a translational fusion between the transit peptide and the coding sequence, and the Cys-Met amino acid sequence at the junction must be maintained.

Figure 2:
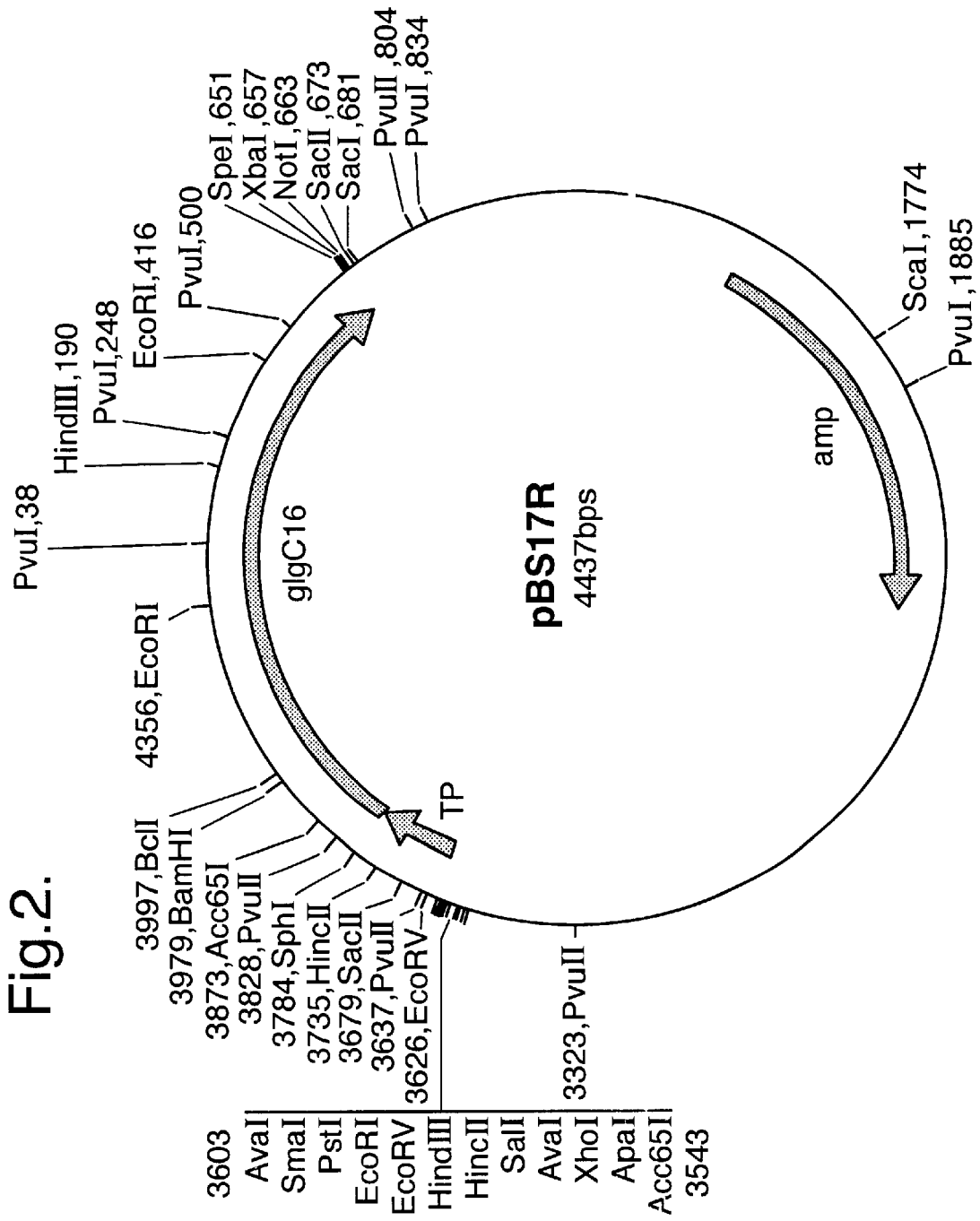
FIG. 2 shows a map of the plasmid pBS17R used in the sticky-feet polymerase chain reaction.

We have previously used pJIT117 to attach the ssu transit peptide to the coding sequence for *E. coli* ADPG PPase glgC16 using restriction digestion and PCR. The TP-glgC16 DNA, herein known as SEQ. ID. No. 1, was subsequently transferred to the vector pBluescript (Stratagene I,td., Cambridge UK) to create pBS17R (the map for which is shown in FIG. 2) and this plasmid was useful in generating a similar construct for glgA.

The glgA coding sequence has no convenient restriction sites at the 5'-end. Therefore, to ensure that the open reading frame was in a translational fusion with the ssu transit peptide and to maintain the integrity of the Cys-Met cleavage site, plasmid pBS17R was used to substitute the glgA sequence for the glgC16 sequence with a technique called sticky-feet PCR (Clackson and Winter, 1989).

Figure 3:
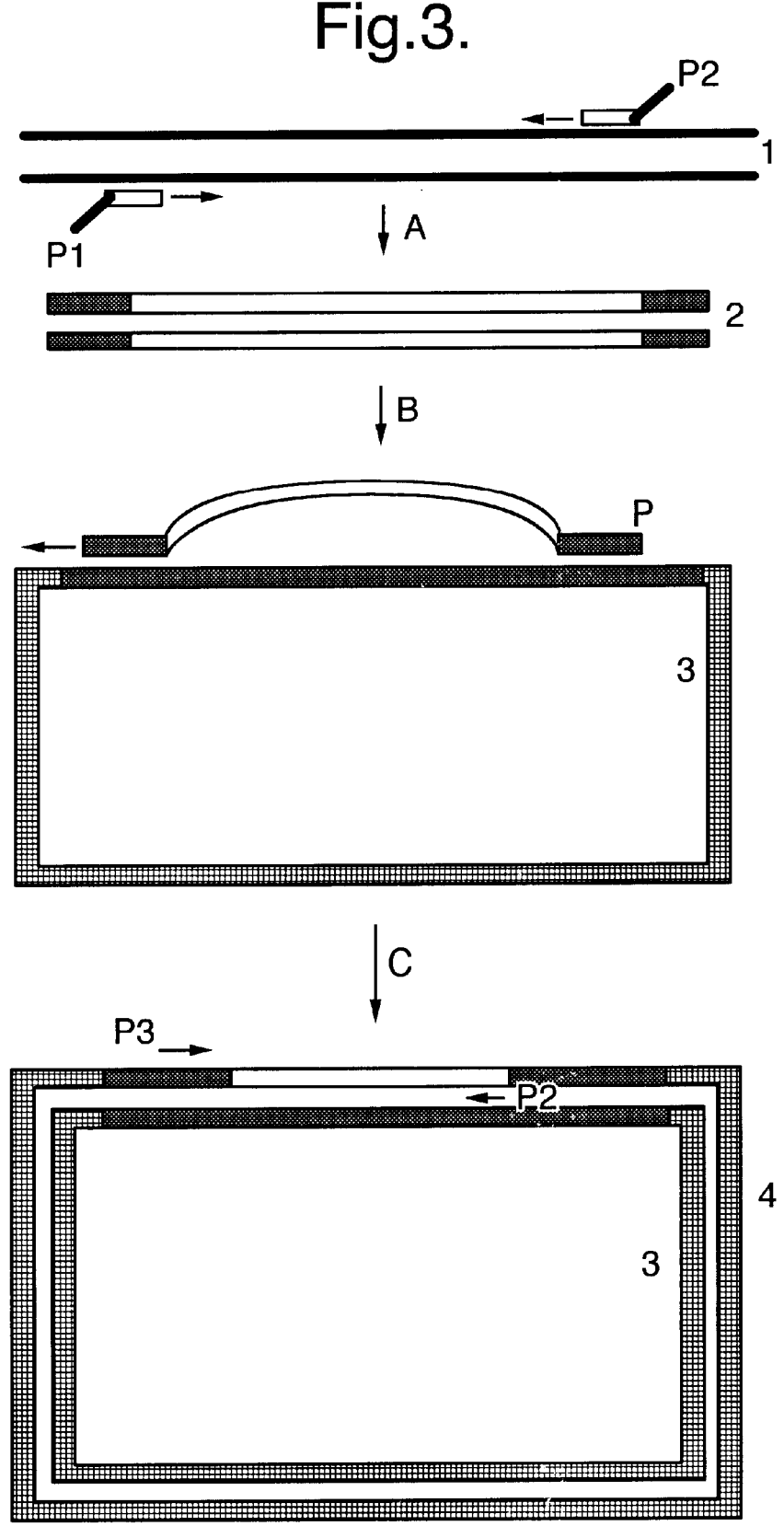
FIG. 3 shows a diagrammatic representation of the steps in the sticky-feet polymerase chain reaction.

This technique is explained diagrammatically with reference to FIG. 3. In this technique, PCR primers are designed to the 5' and 3' ends of the acceptor sequence of chromosomal or genomic DNA and the sequences which are to be attached to the acceptor from a donator plasmid. In Step A, PCR is used to amplify the sequences which are to be inserted in the donator. In Step B the amplified acceptor DNA fragment is annealed to the donator plasmid which has been made single-stranded and carries uracil residues instead of thymidine residues by using a specific type of *E. coli* host. In Step C, a new strand is synthesized, using the donator plasmid as template and the acceptor fragment as primer, with a combination of Taq polymerase, T7 DNA polymerase (Sequenase) and T4 DNA ligase. The new double-stranded plasmid is a hybrid with one strand of the uracil-containing donator and one strand incorporating the acceptor fragment.

This hybrid plasmid is then transferred into a normal *E. coli* host where the uracil-containing strand is degraded and the acceptor strand replicated. A double-stranded plasmid incorporating the acceptor DNA can then be recovered. As an alternative, in Step D (not shown), the hybrid plasmid can be used in a PCR reaction with primers which will amplify out the acceptor DNA with the required fragments from the donator attached.

In this particular example, glgA sticky-feet primers were designed as follows:

SEQ. ID. No. 3 GLGASF5 (P1)
T G G T G G A A G A G T A A A G T G C A T G C A G-GTTTTACATGTATGTTCA
←ssu TP 3' end|glgA 5' end→

SEQ. ID. No. 4 GLGASF3 (P2)
T C G C T C C T G T T T A T G C C C T A G A T C T C-TATTTCGAGCGATAGTAAAGCTCACGGT
←glgC 3' end|glgA 3' end→

The PCR primers are designed to the 5' and 3' ends of the glgA cDNA sequence.

The 5' end primer (SEQ. ID. No.3) also has sequences which are homologous to the ssu-TP.

The 3' end primer.(SEQ. ID. No.4) also incorporates sequences which are homologous to the 3' end of the glgC coding sequence These primers arc used in a PCR process to amplify a glgA fragment with extensions which will overlap onto the sequences in pBS17R. This is represented by Step A of FIG. 3.

Plasmid pBS17R. is made into a template for sticky-feet PCR by transferring the plasmid into the *E. coli* host CJ236 (Raleigh et al., 1989). This host is deficient in the enzyme dUTPase, (i.e., dut) which results in deoxyuridine being incorporated into the DNA instead of thymidine. The absence of another enzyme uracyl N-glycosylase (ung) means that the deoxyuridines cannot then be removed from the DNA.

In Step B of FIG. 3, the extended glgA DNA (2) is annealed to the uracil-containing template which has been isolated as single-stranded DNA (3), and a new strand is synthesized as per Step C above. The new double-stranded plasmid is a hybrid (5) with one strand of the uracil-containing template (3) and the other strand consisting of the plasmid backbone and the glgA fragment now with ssu-TP and a 3' glgC fragment attached at 5' and 3' ends respectively (4).

In Step D (not shown), the hybrid plasmid is used in a PCR reaction with primers (SEQ. ID. No. 5) (P3) (see below) and SEQ. ID. No. 4 (P2) which will amplify out the extended glgA.

With reference to FIG. 3, the experimental details are as follows:

The primers GLGASFS (P1) (SEQ. ID. No. 3) vs GLGASF3 (P2) (SEQ. ID. No. 4) were kinased and used to amplify the glgA open reading frame with extension sequences using *E. coli* LCB618 genomic DNA (1) as template. The DNA (2) was purified with GeneClean (BIO 101, Ltd.). The sticky-feet template DNA, single-stranded uracil pBS17R DNA (3), was isolated from 5 ml overnight cultures of the dut- ung- *E. coli* strain CJ236.

The sticky-feet PCR reaction was carried out in 10 ul volume containing 20 ng ss uracil pBS17R (3); 200 ng glgA DNA (2), 1 ul×10 Taq polymerase buffer, 1.0 ul 2 mM mixture of dATP, dTTP, dCTP, dGTP (2 mM dNTPs); 2.5 units Taq polymerase. The mix-was overlaid with 30 ul mineral oil and cycled once at 94° C., 3 min; 72° C., 2 min; 40° C., 2 min and then cooled to room temperature. 10 ul of a solution containing 2.0 ul×5 Sequenase buffer (200 mM Tris-HCl pH 7.5; 100 mM $MgCl_2$, 250 mM NaCl), 1.5 ul of 0.1 mM Dithiothreitol (DTT); 2.0 ul 10 mM Adenosine 5' triphosphate (ATP); 4 units T4 DNA ligase; 6.5 units Sequenase was then added and the reaction incubated at room temperature for 30 minutes.

6.1.3. Generation of TP-glgA DNA 1.0 ul of the reaction containing the hybrid plasmid (3+4) was taken and diluted to 10 ul with 10 mM TE at pH8.0. 1.0 ul of the diluted sample was used in a PCR reaction in order to obtain the TP-glgA coding sequence (Step C of FIG. 3). The primers used were TPSSU5 (P3) (SEQ. ID. No. 5) vs GLGASF3 (P2) (SEQ. ID. No. 4).

SEQ. ID. No. 5 TPSSU5 (P3)

ACGTAGATCTATGGCTTCTATGATATCCTCTTC

The primers both have restriction sites for BglII, therefore after purification, the amplified DNA was digested with BglII and subcloned into the BamHI site of pDV03000 (see below).

6.1.4. Construction of pDV03000 Vector

Figure 4:
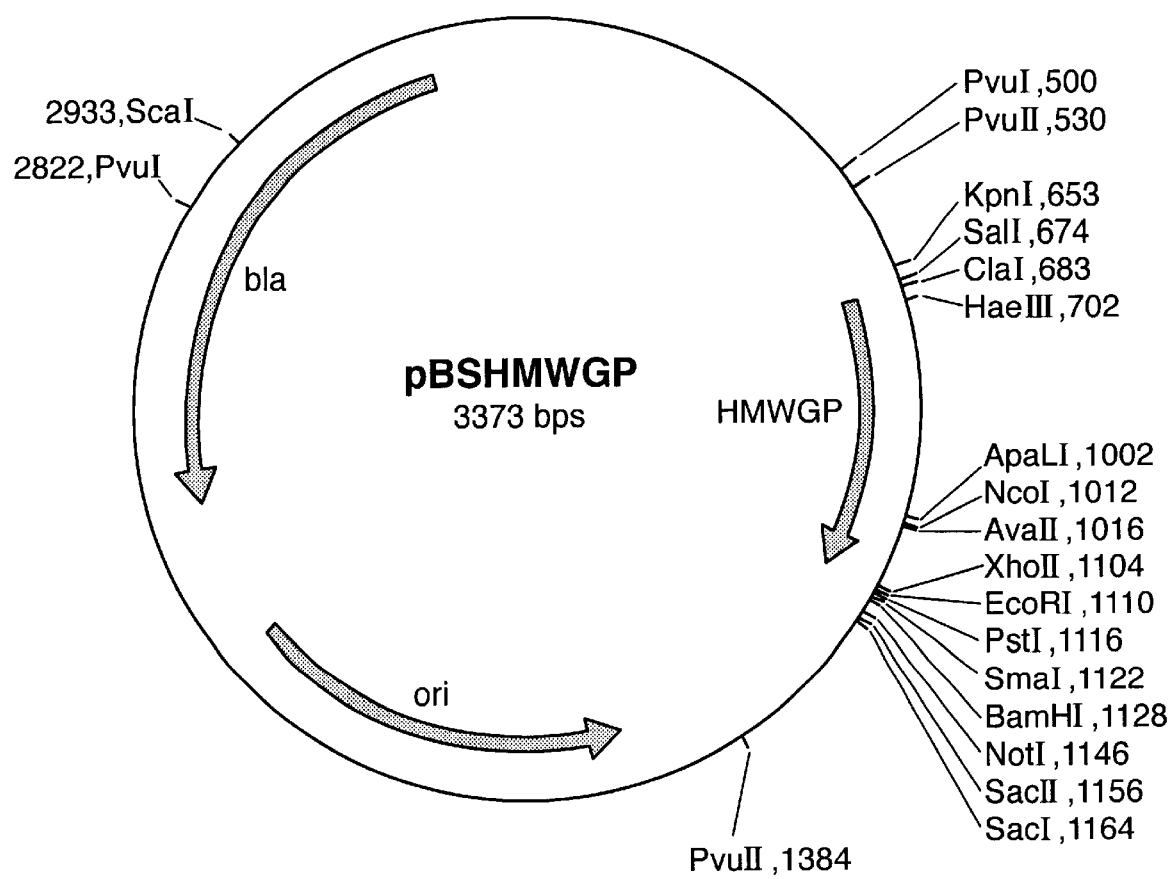
FIG. 4 shows a map of the plasmid pBSHMWGP used in the preparation of the plasmid of FIG. 6.

Transgenic wheat and maize plants are generated by particle bombardment of embryos and it is not necessary to use binary vectors. For expression of the glgA protein the coding sequence is placed under the control of an endosperm-specific promoter. One such suitable promoter is that from the High Molecular Weight Glutenin (HMWG) gene of wheat (Bartels and Thompson, 1986). Primers (P4) and (P5) (SEQ. ID. Nos. 6 and 7 respectively) were designed so that the 430 bp HMWG promoter, (the nucleotide sequence of which is given in SEQ. ID. No. 2) could be isolated by PCR and subcloned via EcoRI and ClaI restriction sites into pBluescript to generate the plasmid pBSHM-WGP (FIG. 4).

Figure 5:
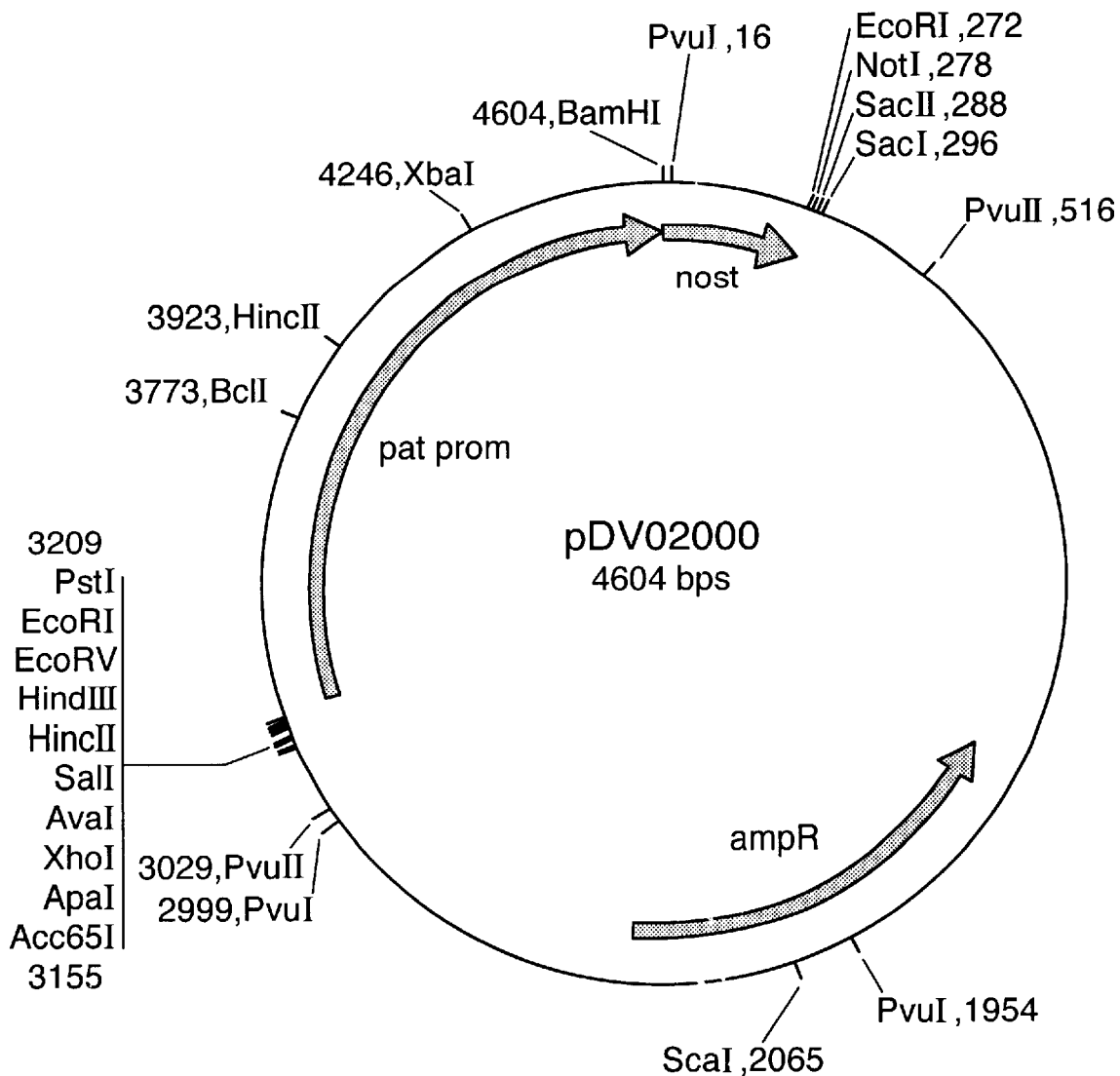
FIG. 5 shows a map of the plasmid pDV02000 used in the preparation of the plasmid of FIG. 6.
Figure 6:
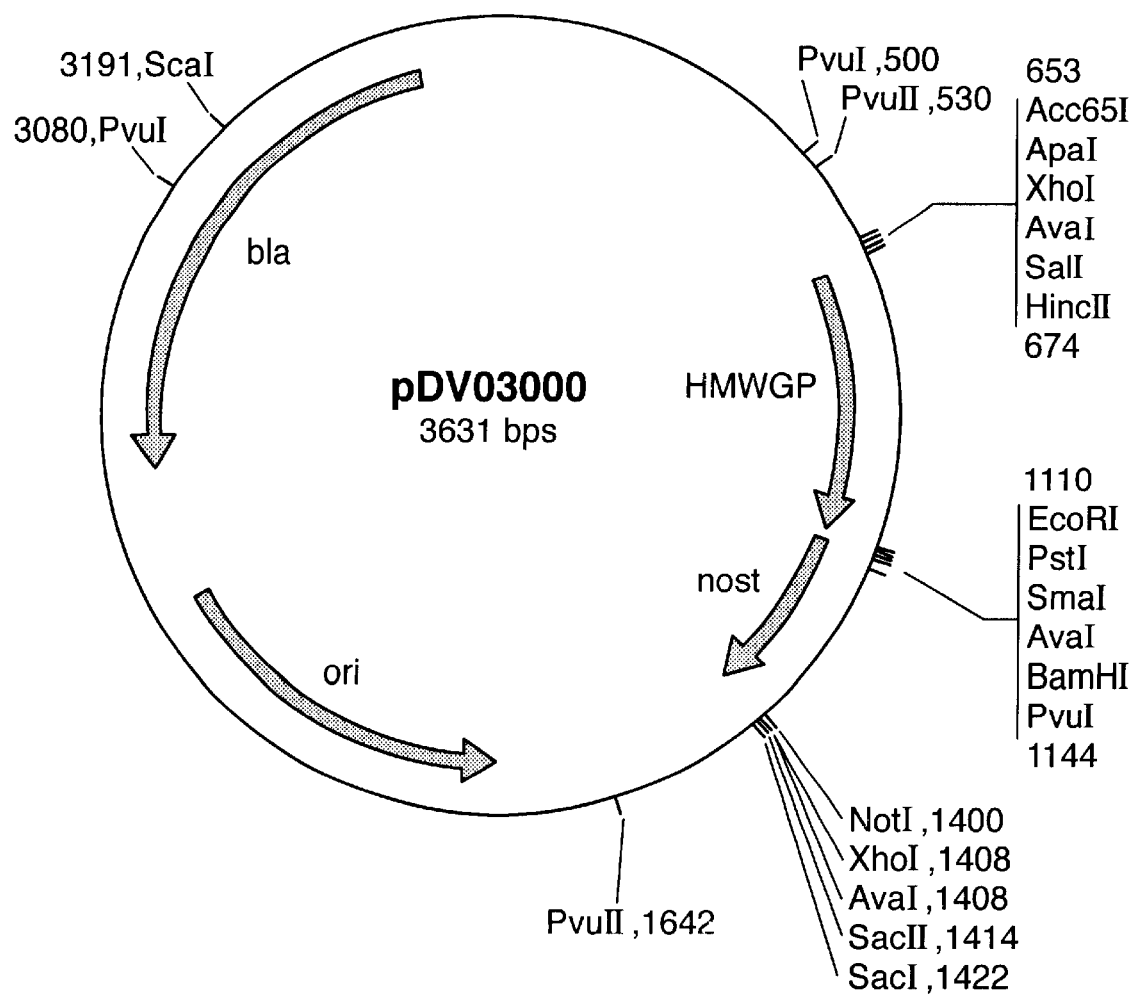
FIG. 6 shows a map of the plasmid pDV03000 used in the preparation of the plasmid of FIG. 7.

A second set of PCR primers were designed to obtain the nopaline synthase terminator from plasmid pDV02000, the map of which is shown in FIG. 5. This plasmid was previously constructed in our laboratory as an intermediate vector for the sub-cloning of coding sequences. The 5' primer, NTPRIME5 (P6) (SEQ. ID. No. 8), has a BarnHI restriction site, while the 3' primer NTP3NXS2 (P7) (SEQ. ID. No. 9), has restriction sites for NotI, XhoI and SacII. The amplified DNA was digested with BamHI and SacII and ligated into the pBSHMWGP plasmid to generate pDV03000 (the map of which is shown in FIG. 6).

SEQ. ID. No. 6 HMWGPRO5 (P4)

GACATCGATCCCAGCTTTGAGTGGCCG-TAGATTTGC

SEQ. ID. No. 7 HMWGPRO3 (P5)

GACGAATTCGGATCTCTAGTTTGTGGT-GCTCGGTGTTGT

SEQ. ID. No. 8 NTPRIME5 I (P6) CAGGATC-CGAATTTCACCCGATCGTTCAAACA

SEQ. ID. No. 9 NTP3NXS2 (P7)

GACCCGCGGCTCGAGGCGGCCGC-CCGATCTAGTAACATAGATGACACCGC pDV03000 vector has the HMWG promoter-nos terminator sequences separated by unique restriction sites for EcoRI, PstI, SmaI and BamHI.

6.1.5. Construction of pDV03191

Figure 7:
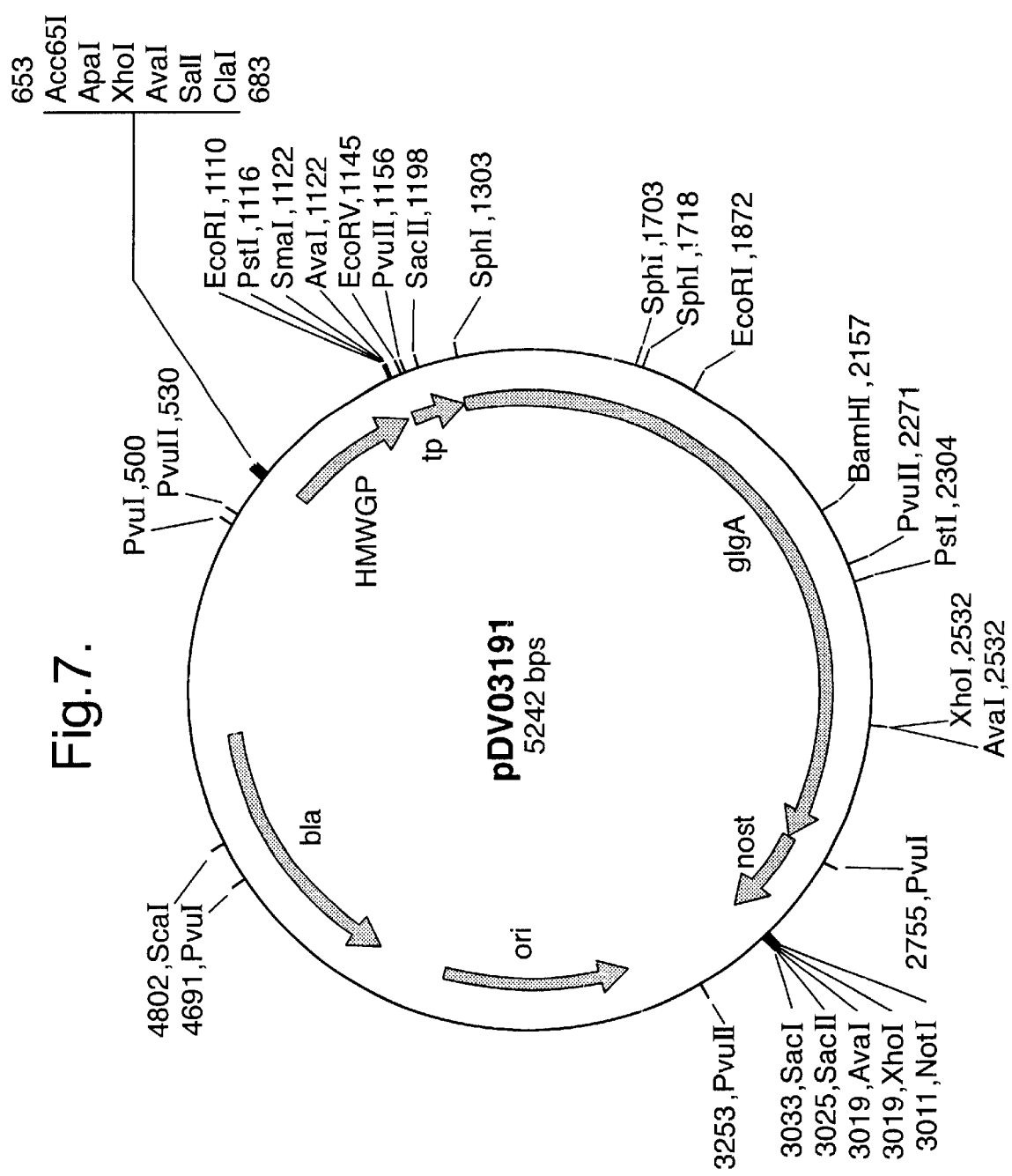
FIG. 7 shows a map of the plasmid pDV03191 according to one aspect of the invention and used in the transformation process of the invention.
Figure 10:
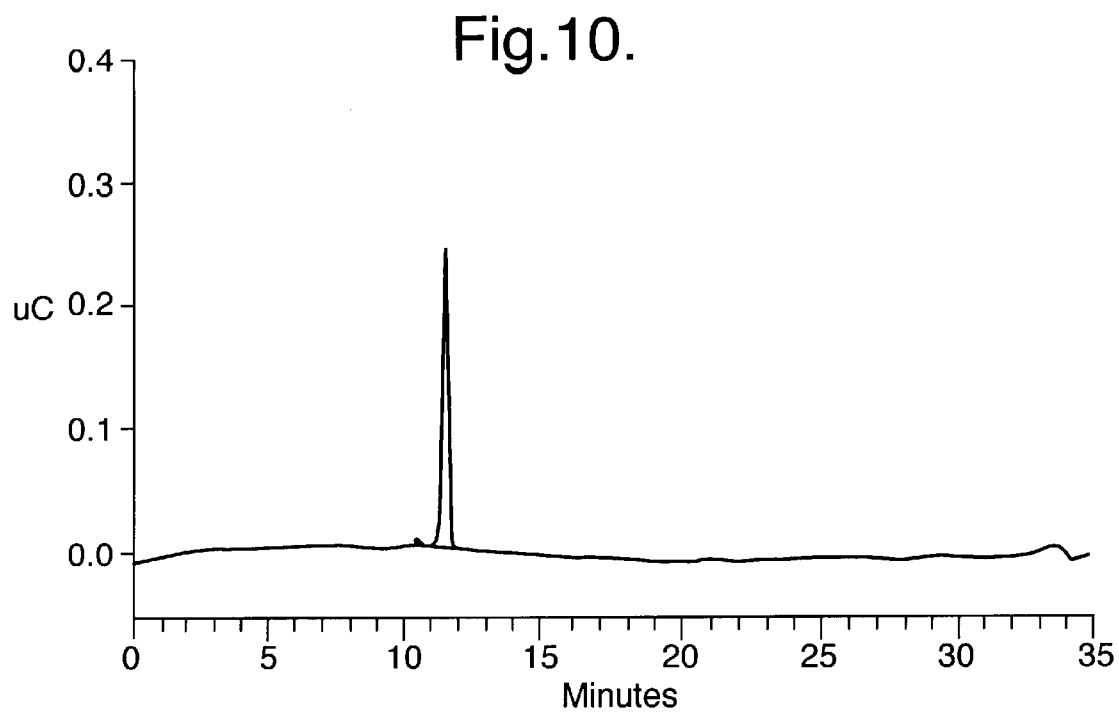
FIG. 10 shows a standard chromatogram of maltotriose at 1 mM concentration.
Figure 11:
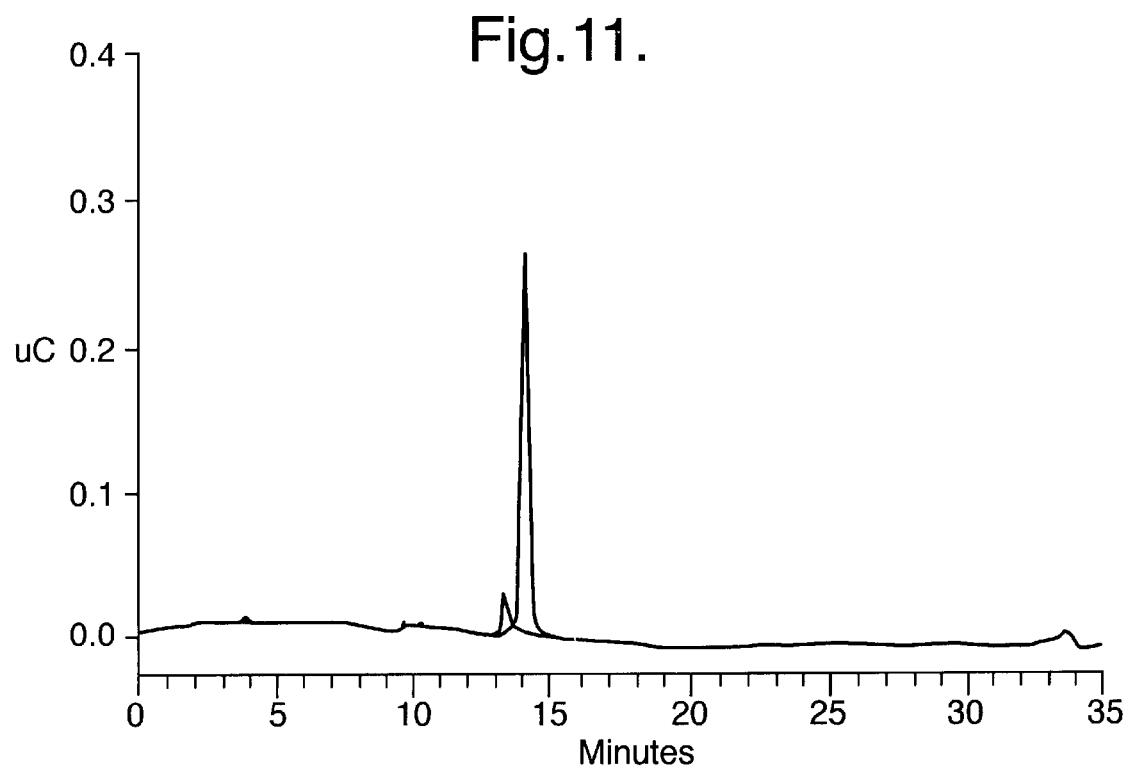
FIG. 11 shows a standard chromatogram of maltohexaose at 1 mM concentration.

TP-glgA DNA amplified from the sticky-feet PCR sample with primers TPSSU5 vs GLGASF3 (Step D, FIG. 3) was digested with BglII, purified and ligated into the BamHI site of pDV03000. Plasmid pDV03191 (the map of which is shown in FIG. 7) was confirmed by restriction enzyme digestion and by sequencing of the junctions between promoter and coding sequence. *E. coli* XL1 Blue (Stratagene Ltd., UK) harboring pDV03191 was deposited by Advanced Technologies (Cambridge) Limited of 210 Cambridge Science Park, Cambridge CB4 OWA, under the Budapest Treaty on the International Recognition of the Deposit of Microorganisms for the purposes of Patent Procedure at the National Collection of Industrial and Marine Bacteria (NCIBM) 23 St. Machar Street, Aberdeen, Scotland, GB on Aug. 4, 1998 under accession number NCIMB 40962. The microorganism is *E. coli* XL1 Blue: strain LCB618 containing pDV03191. The DNA for *E. coli* glgA was inserted as described above. into pBluescript with the ssu transit peptide, the HMWG promoter and nos terminator. The vector is useful for altering starch properties.

6.1.6. Transformation of Wheat

Methods for the transformation of wheat by particle bombardment are well known in the art, for example see Vasil et al., 1992.

Immature embryos of wheat are used to initiate embryogenic callus. The callus is subcultured and used for particle bombardment with gold particles coated with plasmid DNA.

Two plasmids are used per bombardment, one plasmid carries the construct of interest, in this case pDV03191. The second plasmid carries the selectable marker which expresses the gene responsible for resistance to the herbicide Basta. Plants resistant to Basta are generally found to also have the recombinant gene of interest present. Bombarded calli are grown on Basta selection media and surviving calli are transferred to regeneration medium. Rooted plants are transferred to soil and grown to maturity in a growth room.

Primary transformant wheat plants (To) are selfed to produce transgenic seed.

Seed are extracted for protein and the protein analyzed by western blotting for the presence of *E. coli* glgA polypeptide.

Example 2: Biochemical Analysis of glgA Transformed Maize 6.2.1. Expression of glgA Protein Soluble protein samples were prepared from individual maize grain derived 30 from transformed maize plants. Each grain was pulverized in a pestle and mortar until a fine powder was obtained. A portion of this powder (100–200 mg) was placed in an Eppendorf tube and 500 ul of ice cold extraction buffer (50 mM HEPES, pH 8.0; 10 mM DTT; 10 mM EDTA) added. The powder was homogenized with a micropestle to release soluble proteins.

The extract was centrifuged at 13,000 rpm for 1 minute and the supernatant decanted into a fresh Eppendorf tube and stored on ice. The total protein content in the soluble protein sample was assayed using The Bradford dye binding method (Bradford, M. 1976).

An aliquot of the soluble protein sample containing 100 mg total protein was placed into an Eppendorf tube and excess acetone (ca. 1.5 ml) was added to precipitate the proteins. The proteins were collected by centrifuging the sample at 13,000 rpm for 5 minutes. The acetone was decanted off and the samples were air-dried until all the residual acetone had evaporated.

SDS PAGE loading buffer (4% (w/v) SDS; 12% (w/v) glycerol; 50 mM Tris-HCl pH 6.8; 2% (v/v) β-mercaptoethanol; 0.01% Serva blue G) in an amount of 100 ul was added to the protein sample contained in the Eppendorf tube. Samples were boiled for 1 minute before loading onto a polyacrylamide gel. Electrophoresis was carried out according to the method of Schagger and Von Jagow (1987). The resolving gel composition was 10% acrylamide, 3% bis-acrylamide. Gels were run at 50 V constant for 16 hours.

Separated proteins were transferred from the acrylamide gel 1 onto PVDF membrane by electroblotting (Transfer buffer. 20% methanol; 25 mM Tris-HCl pH 8.3; 190 mM glycine. Run in a Biorad blotting apparatus at 50 V for 3 hours).

To detect expression of glgA the membrane was challenged with a rabbit anti-glgA antiserum (raised glgA-GST fusion protein purified from E. coli). Specific cross-reacting proteins were detected using an anti-rabbit IgG-alkaline phosphatase conjugate secondary antibody and visualized by the NBT/BCIP reaction.

6.2.2. NuPAGE™ Electrophoresis

Alternatively, an aliquot of the soluble protein sample, containing 100 mg total protein was placed into an Eppendorf tube and excess acetone (ca. 1.5 ml) was added to precipitate the proteins. The proteins were collected by centrifuging the sample at 13,000 rpm for 5 minutes. The acetone was decanted off and the samples were air-dried until all the residual acetone had evaporated.

NuPAGE™ loading buffer (2% (w/v) SDS; 10% (w/v) sucrose; 25 mM Tris-HCl pH 8.5; 1% (v/v) β-mercaptoethanol; 0.5 mM EDTA; 0.02% Serva blue G250; 0.006% Phenol Red) 100 ul, was added to the protein sample contained in the Eppendorf tube. Samples were heated at 100° C. for 1 minute before loading onto a polyacrylamide gel. Electrophoresis was carried out on NuPAGE™ precast gels according to the manufacturer's instructions (Novex, San Diego Calif.). Gels were run at 200 V constant for 60 minutes using MES SDS running buffer (20 mM MES/20 mM Tris-HCl pH 7.3; 1% (w/v) SDS; 1 mM EDTA).

Separated proteins were transferred from the acrylamide gel onto PVDF membrane by electroblotting (Transfer buffer: 20% methanol; 25 mM Bis-Tris/25 mM Bicine pH 8.3; 1 mM EDTA. Run in a Novex electroblotting apparatus at 25 V for 1.5 hours).

To detect expression of glgA the membrane was challenged with a rabbit anti-glgA antiserum (raised against glgA-GST fusion protein purified from E. coli). Specific cross-reacting proteins were detected using an anti-rabbit IgG-horse Radish Peroxidase conjugate secondary antibody and visualized using enhanced chemiluminesence (ECL) as supplied by Amersham International.

Several transformed lines were found to express a 50 kDa protein in their grain, which was not present in control grain derived from non-transformed maize plants.

6.2.3. Preparation of Wheat Starch

Starch was extracted from grain of separate field grown samples of two of the glgA expressing lines and a control line. Wheat grains of each sample (3–4-g) were placed in a mortar, 30 ml of 1% sodium bisulphite was added and placed on ice for 30 minutes. The grains were then gently pulverized using a pestle. The solution was filtered through a nylon filter sieve and collected in a centrifuge tube. The pulverized wheat grains were re-extracted with a further 30 ml of 1% sodium bisulphite and the filtrates were combined. The filtrate was centrifuged at 6,000 rpm for 5 minutes. After decanting off the supernatant, the pellet of extracted starch was re-suspended in water and centrifuged at 6,000 rpm for 5 minutes. This was repeated once. The resulting starch pellet was re-suspended in acetone, centrifuged at 6000 rpm for 5 minutes and the supernatant decanted away. This was repeated once and the starch left to air dry. Once dried the starch was stored at −20° C.

6.2.4. Branch Chain Length Analysis of Wheat Starch

Portions of the starch samples were digested with isoamylase and the resulting unbranched linear glucan chains were analyzed by HPLC.

75 mg of isolated wheat starch was placed in a 15 ml Pyrex boiling tube and suspended in 3.0 ml of water. The sample was placed in a boiling water bath for 6 minutes, occasionally removed and vortex mixed. The sample was cooled to room temperature and 250 ul of 200 mM sodium acetate, pH 3.5 and 180 units of isoamylase enzyme added. The samples were made up to a final volume of 3.8 ml with water. After mixing, the sample was placed in a 37° C. water bath for 4 hours. The samples were occasionally vortex mixed throughout this incubation period. At the end of the incubation the sample was placed in a boiling water bath for 2 minutes, and then allowed to cool to 4° C. The sample was centrifuged at 3,400 rpm for 20 minutes. The resulting supernatant was transferred to Eppendorf tubes and centrifuged at 13,000 rpm for 15 minutes. Finally, the sample was filtered through a 0.2 mm syringe filter and stored at 4° C. until required.

Separate isoamylase digest samples were normalized to a constant total glucan content by digesting a portion of the sample to glucose using a-amylase and amyloglucosidase.

Two 100 ul aliquots of isoamylase digested starch were placed in two separate Eppendorf tubes (one is to be used as a blank). To one aliquot was added: 500 ul of 200 mM sodium acetate pH 4.8; 50 ul of a-amylase solution containing 10 units of α-amylase; 100 ul of amyloglucosidase solution containing 10 units of amyloglucosidase and water to a final volume of 1.0 ml. To the second (blank) aliquot was added: 500 ul of 200 mM sodium acetate pH 4.8 and 400 ul of water. The samples were left to digest at 25° C. for 16 hours.

The glucose content of the digest and blanks was assayed spectrophotometrically using a coupled enzyme assay. An aliquot of the total glucose digest or the blank was added to a cuvette containing in a final volume of 990 ul 100 mM HEPES, pH 8.0; 5 mM $MgCl_2$ 4 mM NAD; 1 mM ATP and 1 unit of hexokinase. The optical density (OD) of the reaction mixture at 340 nm was measured prior to the addition of 10 ul containing 1 unit of glucose-6-phosphate dehydrogenase. The OD at 340 nm was monitored until there was no further change and the difference in OD after the addition of glucose-6-phosphate dehydrogenase compared to before the addition of glucose-6-phosphate dehydrogenase was determined. This figure was used to determine the total glucose amounts in the original isoamylase digests. These samples were diluted with water to a standard concentration of 8 mM total glucose and stored at 4° C. until required for HPLC analysis.

The samples were then analyzed by Dionex HPLC using a Dionex PA 100 column and PED-Integrated Amperometric detection. The solvent flow rate was 1.0 ml/min and a gradient system was developed. Solvent 1 consisted of 100 mM NaOH and Solvent 2 was 100 mM NaOH, 0.60 M sodium acetate. The gradient profile was as shown in Table 1, with the pulsed electrochemical detection (PED) parameters shown in Tables 2.1 and 2.2.

TABLE 1

Gradient Profile

| Event Start Time (min) | Solvent 1 (%) | Solvent 2 (%) |
|---|---|---|
| 0 | 100 | 0 |
| 1 | 100 | 0 |
| 2 | 100 | 0 |
| 3.0 | 0 | 100 |
| 30.1 | 100 | 0 |
| 35 | 100 | 0 |

TABLE 2.1

Waveform Table

| Time (sec) | Potential (V) |
|---|---|
| 0 | 0.1 |
| 0.5 | 0.1 |
| 0.51 | 0.6 |
| 0.59 | 0.6 |
| 0.6 | −0.6 |
| 0.65 | −0.6 |

TABLE 2.2

Integration

| 0.3 | 0.5 |
|---|---|

Three isoamylase digestions were performed for each sample and three aliquots of each isoamylase digest were analyzed by the HPLC system. Separate chromatogram peaks were assigned to specific linear glucan sizes by reference to standard mixtures containing linear glucans of known numbers of glucose molecules (see FIGS. 8–12). Peak areas were abstracted from the primary data and averaged for the replicate chromatograms.

Figure 15:
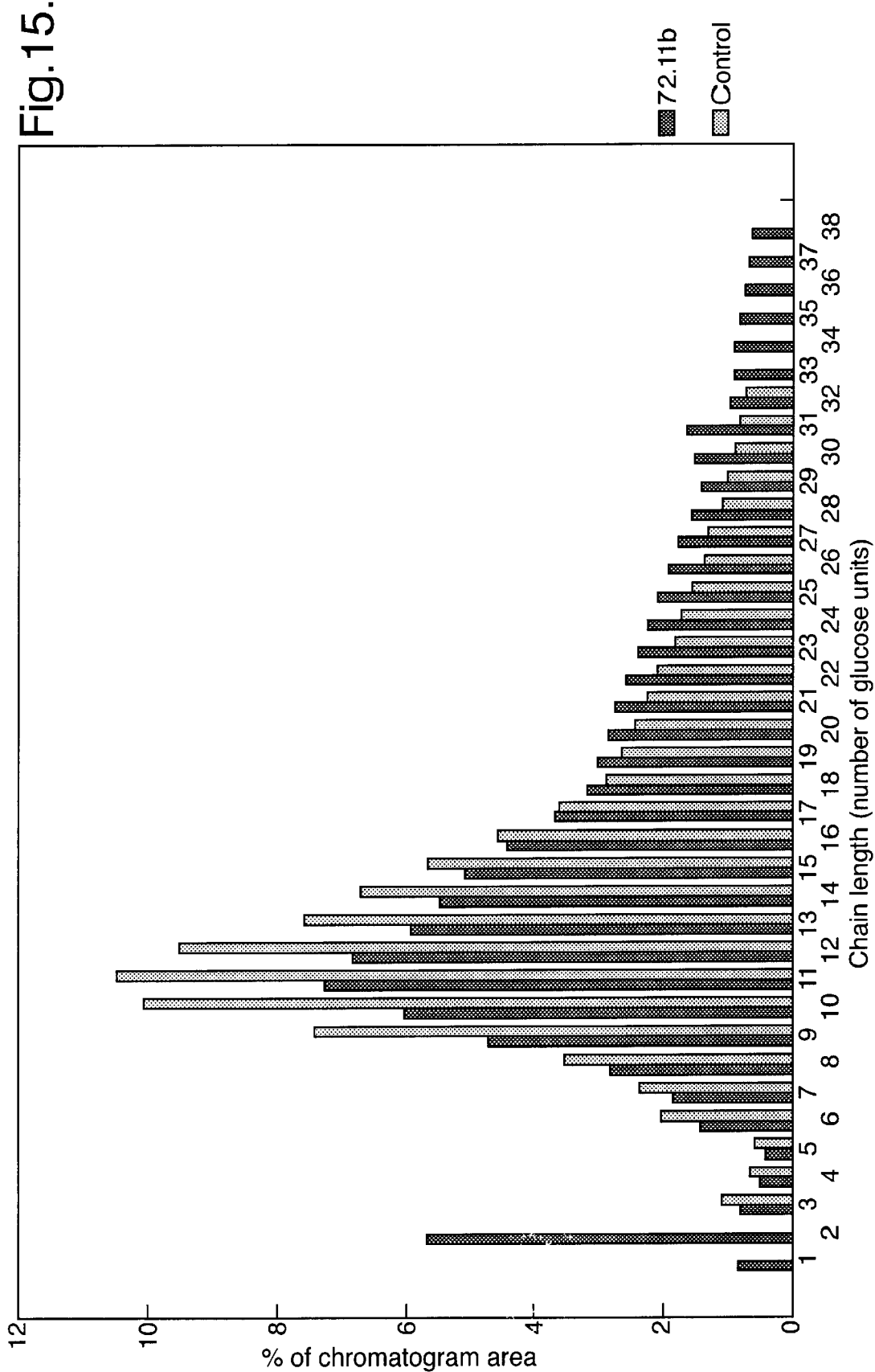
FIG. 15 shows a graph of starch branch chain lengths for starch from the seed of a further single transgenic wheat plant compared with starch from the seed from a control wheat plant.
Figure 16:
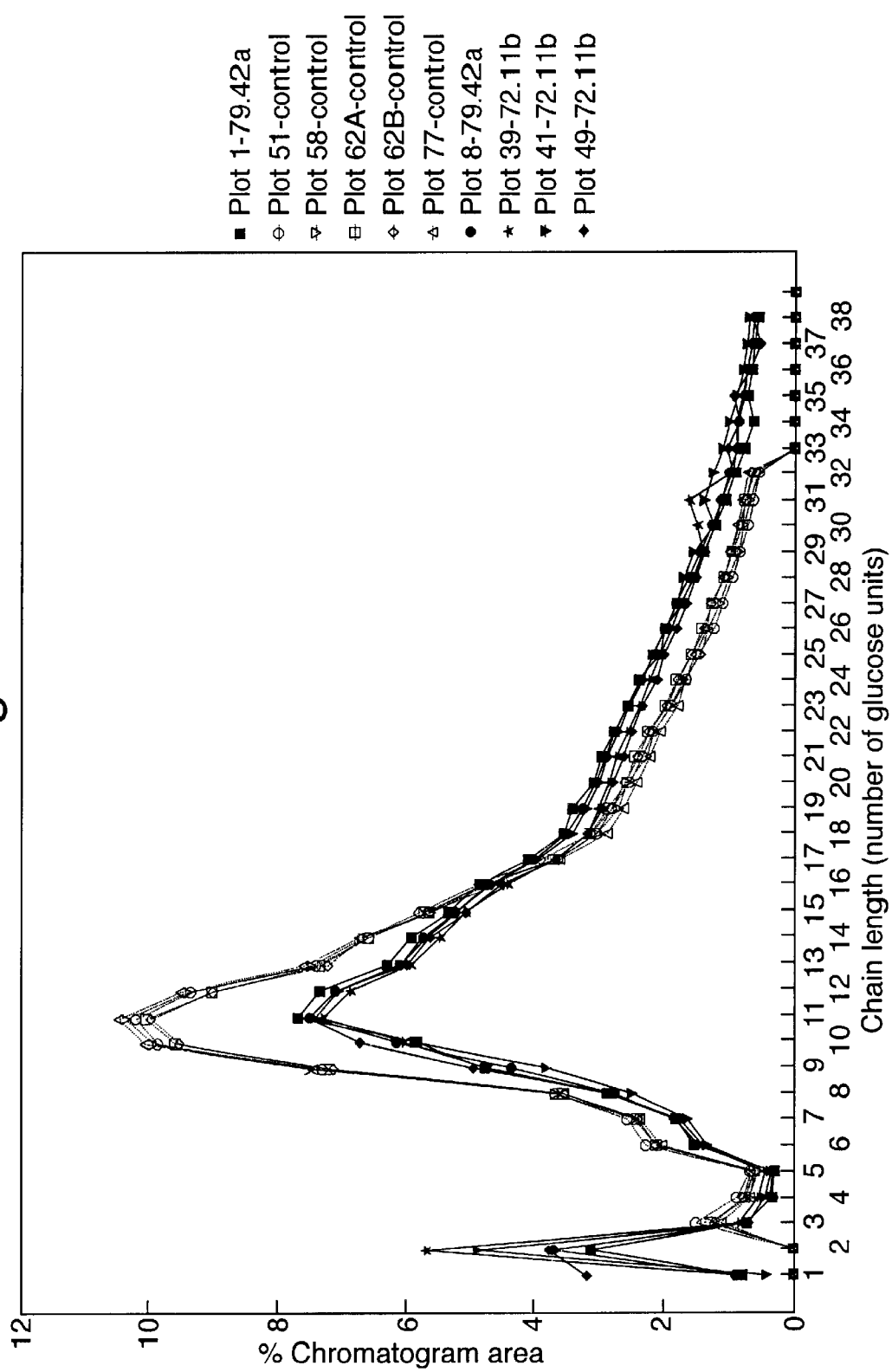
FIG. 16 shows a comparison of branch chain length for a family of starches from the seed of transgenic lines against a family of starches from the seed of control wheat plants.

FIGS. 8 to 12 are HPLC traces of standards for various sugars. The standards in FIGS. 8–12 allow the peak area for each peak of the inventive sample of FIG. 13 to be converted to a quantitative representation of the number of glucan chains in each peak, and the position (on the x-axis) of each peak to the number of glucose residues in each chain, i.e., the chain length. In FIGS. 14 and 15 this conversion has been done for wheat starch extracted from a single transgenic line and its paired control. In FIG. 16, a family of starches from transgenic lines are compared with a family of controls. FIG. 16 clearly shows that the transgenic starches have a different chain length distribution from the control starches. The starch in the transgenic seed has a lower percentage of polysaccharide in the chain lengths between 6 and 15 glucose units and an increase in the percentage polysaccharide in the chain length between 17 and 28 glucose units. There is thus an average increase in chain length in the population. The starch has therefore been altered, which alteration affects its processing capabilities.

Example 3: Maize Plants Transformed with glgA Recombinant Gene

In the transformation step, immature maize embryos are used instead of wheat and are subject to particle bombardment with gold particles coated with plasmid DNA. Methods for the transformation of maize are well known in the art, for example see Gordon-Kamm et al., (1990) and Fromm et al., (1990).

After rooted primary transformant plants (To) are transferred to soil and grown to maturity, maize plants are back-crossed to produce transgenic seed which can be extracted and analyzed according to Example 2. Further back-crossing is performed to introgress the transgene into elite varieties and self ing of transgenic plants is performed to obtain plants and seed which are homozygous for the transgene. Seed from these generations can also be extracted and analyzed according to method 2.

Seed from a number of back-crossed primary transformants were shown to be expressing the glgA protein. The plants grown up from the remaining seeds were subsequently selfed and progeny seed were extracted for protein and western blotting according to Example 2. FIG. 17 shows the presence of glgA polypeptide in seed from two of these second generation lines 2-AN4-5'-2 and 2-AM4-6'-1.

Example 4: Viscometry Measurements of Transgenic Wheat Seed Extracts

Flour was extracted from T2 and T3 progeny seed of primary transformant wheat line 72.IIB which was shown to be expressing the glgA polypeptide by western blots. 4 g of ground sample (14% moisture) was mixed with 25 ml water or with 24.5 ml water+0.5 ml 10% AgNO$_3$ solution. The presence of silver nitrate will inhibit any amylase activity in the slurry and allows the true viscosity developed by the flour to be assessed.

The slurry was subject to rapid viscometric analysis (RVA) using standard profile 1 (Table 3). Results of the RVA are tabulated in Table 4 and Table 5 below.

Standard 1: Idle temperature: 50±1 W

End Test (HH:MM:SS): 00:13:00

TABLE 3

| Time (HH:MM:SS) | Type | Value |
|---|---|---|
| 00:00:00 | Speed | 960 rpm |
| 00:01:00 | Speed | 160 rpm |
| 00:01:00 | Temp. | 50° C. |
| 00:04:45 | Temp. | 95° C. |
| 00:07:15 | Temp. | 95° C. |
| 00:11:00 | Temp. | 50° C. |

TABLE 4

RVA STD without AgNO$_3$

| | Pasting temperature | Peak viscosity | BKD | Final viscosity |
|---|---|---|---|---|
| CYMMIT control | 87.2 | 191 | 61 | 222 |
| 72.11B/62 | 87.2 | 181 | 57 | 208 |
| 72.11B/39/4 | 88.1 | 182 | 53 | 223 |
| 72.11B/49/11 | 86.3 | 184 | 53 | 230 |
| 72.11B/41/22 | 88.1 | 185 | 52 | 226 |

TABLE 5

RVA Modified with AgNO₃

| | Pasting temperature | Peak viscosity | BKD | Final viscosity | Peak AgNO₃-Peak standard | Final viscosity AgNO₃-FV std |
|---|---|---|---|---|---|---|
| CYMMIT ctrl | 86.4 | 251 | 98 | 267 | 60 | 45 |
| 72.11B/62 | 87.2 | 251 | 99 | 259 | 70 | 51 |
| 72.11B/39/4 | 87.3 | 238 | 86 | 265 | 56 | 42 |
| 72.11B/49/11 | 87.2 | 234 | 80 | 267 | 50 | 37 |
| 72.11B/41/22 | 86.5 | 244 | 87 | 273 | 59 | 47 |

There is thus a fall in the peak viscosity and final viscosity of flour from the transgenic seeds, even after the influence of amylase has been taken into account. The RVA method is described in Edwards et al., (1999).

Example 5: Differential Scanning Calorimetry (DSC) of glgA Transgenic Wheat Seed Extract Wheat kernels were cleaned and water was added to the sample (90 mg). The sample was allowed to condition in the analysis chamber at ambient temperature for 24 hours before cycling using the following conditions:

Stabilization: 1 h 25 min at 25° C.
Raise temperature to 110° C. at 1.2° C./minute
Cool to 25° C. at 1.2° C./minute.

The DSC results are shown in Table 6.

TABLE 6

| | Peak 1 (amylopectin) | | | Peak 2 (amylose-lipid complex) | | |
|---|---|---|---|---|---|---|
| | Onset Point | Temp. peak | Enthalpy | Onset Point | Temp. Peak | Enthalpy |
| CYMMIT ctrl. | 52 | 60 | 6.9 | 80.2 | 92.5 | 1.9 |
| 72.11B/62 | 52 | 59 | 6.7 | 82 | 93 | 1.4 |
| 72.11B/39/4 | 52 | 60 | 6.8 | 80 | 93 | 1.9 |
| 72.11B/49/11 | 52.3 | 59.6 | 6.4 | 80 | 93 | 1.8 |
| 72.11B/41/22 | 51.7 | 59.4 | 6.8 | 80.2 | 92 | 1.8 |

There is a slight increase in enthalpy values for the transgenic seed extracts.

The DSC method is described in the book of Frazier et al., (1997).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

REFERENCES

The following references are incorporated into the specification by reference in their entireties.

Baecker, P. A., Preston, A., Furlong, C. E. and Preiss, J. (1983) Biosynthesis of bacterial glycogen. Primary structure of E. coli ADPG glucose synthetase as deduced from the nucleotide sequence of the glgC gene. J. Biol. Chem. 258(8), 5084–5088.

Bartels, D. and Thompson, R. D. (1986). Synthesis of messenger RNAs coding for abundant endosperm proteins during wheat-grain development. Plant Sci., 46 (2) 117–125.

Bradford, M. (1976) A rapid and sensitive method for the quantitation of microgram quantities of protein utilizing the principle of protein dye binding. Anal. Biochem. 72, (1–2), 248–254.

Cheng, M., Fry, J. E., Pan, S. Z., Zhou H. P., Hironaka C. M., Duncan D. R., Conner, T. W., and Wan, Y. C. (1997) Genetic transformation of wheat mediated by Agrobacterium tuinefaciens. Plant Physiology, 115 (3), 971–980.

Clackson, T. and Winter, G. (1989). "Sticky-Feet"-directed mutagenesis and its application to swapping antibody domains. Nucl. Acids Res., 17, 10163–10170.

Echt, C. S. and Schwarz, D. (1981). Evidence for the inclusion of controlling elements within the structural gene at the waxy locus in maize. Genetics, 99, 275–284.

Edwards, E., Fulton, D. C., Hylton, C. M., Jobling, S. A., Gidley, M., Rossner, U., Martin, C. and Smith, A. M. (1999). A combined reduction in activity of starch synthases II and III of potato has novel effects on the starch of tubers. Plant J., 17, 251–161.

Frazier, P. J., Donal, A. M. and Richmond, P. Starch: Structure and Functionality (1997). Royal Society of Chemistry, Cambridge, UK.

Fromm, M. E., Morrish, F., Armstrong, C., Williams, R., Thomas, J. and Klein, T. M. 1990). Inheritance and expression of chimeric genes in the progeny of transgenic maize plants. Bio/Technology,8 9), 833–839.

Geurineau, F., Woolston, S., Brooks, L. and Mullineaux, P. (1988). An expression cassette for targeting foreign proteins into chloroplasts. Nucl. Acids Res., 16 (23), 11380.

Gordon-Kamm, W. J., Spencer, T. M., Mangans, M. L., Adams, R. T., Dais, R. J., Start, W. G., O'Brien, J. V., Chambers, S. A., Adams, W. J. et al., (1990). Transformation of maize cells and regeneration of fertile transgenic plants. Plant Cell, 2 (7), 603–618.

Innis, M. A., Gelfand, D. H., Sninsky, J. J. and White, T. J.(1990). PCR Protocols . . . A Guide to Methods and Applications. Published Academic Press.

Kiel, J. A., Boels, J. M., Beldman, G. and Venema, G. (1994). Glycogen in Bacillus subtilis: molecular characterization of an operon encoding enzymes involved in glycogen biosynthesis and degradation. Mol. Microbiol., 11(1), 203–218.

Kuipers, A. G. J; Jacobsen, E; Visser, R. G. F., (1994). Formation and deposition of amylose in the potato tuber starch granule are affected by the reduction of granule-bound starch synthase gene expression. Plant Cell, 6(1), 43–52.

Kumar, A., Larsen, C. E., Preiss, J. (1986). Biosynthesis of bacterial glycogen primary structure of E. coli ADP-glucose α1,4-glucan, 4-glucosyltransferase as deduced from the nucleotide sequence of the glgA gene. J. Biol. Chem., 261 (34), 16256–16259.

Leung, P., and Preiss J. (1987). Cloning ADP glucose pyrophosphorylase glgC with glycogen synthase glgA structural genes from Salmonella-typhimurium. J. Bacteriol., 169 (9), 4349–4354.

Raleigh, E. A., Lech, K., and Brent, R. (1989). Current Protocols in Molecular Biology, Eds. Ausubel F. M. et al., Publishing Associates and Wiley Interscience, New York, Unit 1.4 Sambrook, J., Fritsch, E. F. and Maniatis, T. (1989) Molecular Cloning: A Laboratory Manual. Publd. Cold Spring Harbor, U.S.A. Schagger and Von Jagow (1987). Tricine-SDS-Polyacrylamide gel electrophoresis for the separation of proteins in the range from 1–100 kDA. Anal. Biochem., 166(2), 368–379.

Shewmaker, C. K; Boyer, C. D; Wiesenborn, D. P; Thompson, D. B; Boersig, M. R; Oakes, J. V. (1994). Expression of *Escherichia coli* glycogen synthase in the tubers of transgenic potatoes (*Solanuin tuberosum*) results in a highly branched starch. Pl. Physiol, 104(4), 1159–1166.

Uttaro, A. D. and Ugalde, R. A. (1994). A chromosomal cluster of genes encoding ADP-glucose synthetase, glycogen synthase and phosphoglucomutase in *Agrobacterium turnefaciens*. Gene, 150(1), 117–122.

Vasil, V., Castillo, A. M., Fromm, M. E. and Vasil, I. K. (1992). Herbicide-resistant transgenic wheat plants obtained by microprojectile bombardment of regenerable embryogenic callus. Bio/Technology, 10(6), 667–674.

Visser, G. F.; Stolte, A; Jacobsen, E, (1991). Expression of a chimeric granule bound starch synthase-GUS gene in transgenic potato plants. Plant Mol. Biol, 17 (4), 691–699.

Visser, R. G. F.; Somhorst, I.; Kuipers, G. J.; Ruys, N. J., Feenstra, W. J.; Jacobsen, (1991 a). Inhibition of the expression of the gene for granule bound starch synthase in potato by antisense constructs. Mol. Gen Genet., 225 (2), 289–296.

What is claimed is:

1. Modified starch molecules obtained from wheat or maize plants produced by a method comprising:
   (a) introducing a chimeric gene comprising a promoter, a nucleic acid encoding glycogen synthase, and a terminator, into maize or wheat plant cells such that the maize or wheat plant cells produce modified starch molecules; and
   (b) regenerating a maize or wheat plant from the plant cells to which were introduced the chimeric gene;

wherein the amylopectins of the modified starch molecules have an increased average chain length relative to the amylopectins of starch molecules of a maize or wheat plant lacking the chimeric gene.

2. The modified starch molecules obtained from wheat or maize plants according to claim 1 wherein the increase in average chain length is accompanied by an increase in the percentage of amylopectin chains consisting of 17 or more glucose units.

3. The modified starch molecules obtained from wheat or maize plants according to claim 1 wherein the increase in average chain length of amylopectins is accompanied by a decrease in the percentage of amylopectin chains consisting of 6 to 15 glucose units.

4. The modified starch molecules obtained from wheat or maize plants according to claim 1 wherein there is an increase in the percentage of amylopectin chains between 17 and 38 glucose units.

5. The modified starch molecules according to claim 1, 2, 3, or 4, wherein the modified starch molecules displays decreased viscosity.

6. The modified starch molecules according to claim 1, 2, 3, or 4, wherein the modified starch molecules displays an altered degree of retrogradation.

7. The modified starch molecules according to claim 1, 2, 3, or 4, wherein the modified starch displays an improvement in freeze-thaw stability.

8. The modified starch molecules of claim 1 wherein the nucleic acid encoding glycogen synthase is derived from an unicellular organism.

9. The modified starch molecules of claim 1 wherein the glycogen synthase is derived from *E. coli*, a Agrobacterium species, a Salmonella species or a Bacillus species.

10. The modified starch molecules of claim 1 wherein the promoter is capable of directing expression of the chimeric gene in a particular tissue of the plant and/or at particular stages of development of the plant.

11. The modified starch molecules of claim 1 wherein the promoter directs expression of the chimeric gene to the endosperms of the maize or wheat plants.

12. The modified starch molecules of claim 1 wherein the promoter is the promoter of a wheat high molecular weight glutenin gene.

13. The modified starch molecules of claim 1 wherein the promoter is a promoter selected from the group consisting of the promoter of the gene encoding gliadin, branching enzyme, ADPG pyrophosphorylase, starch synthase, and actin.

14. The modified starch molecules of claim 1 wherein the chimeric gene further comprises a nucleotide sequence encoding a transit peptide or a combination of transit peptides which provides for translocation of the glycogen synthase expressed in the plant cells to a plastid.

15. The modified starch molecules of claim 1 wherein the transit peptide is selected from the group consisting of the transit peptide for the small subunit of the ribulose biphosphate carboxylase enzyme from pea, the transit peptide for the small subunit of the ribulose biphosphate carboxylase enzyme from maize, the transit peptide for the small subunit of the ribulose biphosphate carboxylase enzyme from sunflower, the transit peptide for the plant plastid acyl carrier protein, and the transit peptide for granule-bound starch synthase I.

\* \* \* \* \*

SEQUENCE LISTING

<160> NUMBER OF SEQ ID NOS: 10

<210> SEQ ID NO 1
<211> LENGTH: 1467
<212> TYPE: DNA
<213> ORGANISM: Artificial Sequence
<220> FEATURE:
<221> NAME/KEY: CDS
<222> LOCATION: (1)..(171)
<223> OTHER INFORMATION: Pea ssu transit peptide
<221> NAME/KEY: CDS
<222> LOCATION: (172)..(1467)
<223> OTHER INFORMATION: E. coli glgC16
<223> OTHER INFORMATION: Description of Artificial Sequence: Pea ssu TP
      linked to E. coli glgC16 CDS

<400> SEQUENCE: 1

```
atg gct tct atg ata tcc tct tca gct gtg act aca gtc agc cgt gct        48
Met Ala Ser Met Ile Ser Ser Ser Ala Val Thr Thr Val Ser Arg Ala
 1               5                  10                  15 tct acg gtg caa tcg gcc gcg gtg gct cca ttc ggc ggc ctc aaa tcc        96
Ser Thr Val Gln Ser Ala Ala Val Ala Pro Phe Gly Gly Leu Lys Ser
             20                  25                  30 atg act gga ttc cca gtt aag aag gtc aac act gac att act tcc att       144
Met Thr Gly Phe Pro Val Lys Lys Val Asn Thr Asp Ile Thr Ser Ile
         35                  40                  45 aca agc aat ggt gga aga gta aag tgc atg ctt agt tta gag aag aac       192
Thr Ser Asn Gly Gly Arg Val Lys Cys Met Leu Ser Leu Glu Lys Asn
     50                  55                  60 gat cac tta atg ttg gcg cgc cag ctg cca ttg aaa tct gtt gcc ctg       240
Asp His Leu Met Leu Ala Arg Gln Leu Pro Leu Lys Ser Val Ala Leu
 65                  70                  75                  80 ata ctg gcg gga gga cgt ggt acc cgc ctg aag gat tta acc aat aag       288
Ile Leu Ala Gly Gly Arg Gly Thr Arg Leu Lys Asp Leu Thr Asn Lys
                 85                  90                  95 cga gca aaa ccg gcc gta cac ttc ggc ggt aag ttc cgc att atc gac       336
Arg Ala Lys Pro Ala Val His Phe Gly Gly Lys Phe Arg Ile Ile Asp
            100                 105                 110 ttt gcg ctg tct aac tgc atc aac tcc ggg atc cgt cgt atg ggc gtg       384
Phe Ala Leu Ser Asn Cys Ile Asn Ser Gly Ile Arg Arg Met Gly Val
        115                 120                 125 atc acc cag tac cag tcc cac act ctg gtg cag cac att cag cgc ggc       432
Ile Thr Gln Tyr Gln Ser His Thr Leu Val Gln His Ile Gln Arg Gly
    130                 135                 140 tgg tca ttc ttc aat gaa gaa atg aac gag ttt gtc gat ctg ctg cca       480
Trp Ser Phe Phe Asn Glu Glu Met Asn Glu Phe Val Asp Leu Leu Pro
145                 150                 155                 160 gca cag cag aga atg aaa ggg gaa aac tgg tat cgc ggc acc gca gat       528
Ala Gln Gln Arg Met Lys Gly Glu Asn Trp Tyr Arg Gly Thr Ala Asp
                165                 170                 175
```

-continued

```
gcg gtc acc caa aac ctc gac att atc cgt cgt tat aaa gcg gaa tac      576
Ala Val Thr Gln Asn Leu Asp Ile Ile Arg Arg Tyr Lys Ala Glu Tyr
            180                 185                 190 gtg gtg atc ctg gcg ggc gac cat atc tac aag caa gac tac tcg cgt      624
Val Val Ile Leu Ala Gly Asp His Ile Tyr Lys Gln Asp Tyr Ser Arg
        195                 200                 205 atg ctt atc gat cac gtc gaa aaa ggt gta cgt tgt acc gtt gtt tgt      672
Met Leu Ile Asp His Val Glu Lys Gly Val Arg Cys Thr Val Val Cys
    210                 215                 220 atg cca gta ccg att gaa gaa gcc tcc gca ttt ggc gtt atg gcg gtt      720
Met Pro Val Pro Ile Glu Glu Ala Ser Ala Phe Gly Val Met Ala Val
225                 230                 235                 240 gat gag aac gat aaa act atc gaa ttc gtg gaa aaa cct gct aac ccg      768
Asp Glu Asn Asp Lys Thr Ile Glu Phe Val Glu Lys Pro Ala Asn Pro
            245                 250                 255 ccg tca atg ccg aac gat ccg agc aaa tct ctg gcg agt atg ggt atc      816
Pro Ser Met Pro Asn Asp Pro Ser Lys Ser Leu Ala Ser Met Gly Ile
        260                 265                 270 tac gtc ttt gac gcc gac tat ctg tat gaa ctg ctg gaa gaa gac gat      864
Tyr Val Phe Asp Ala Asp Tyr Leu Tyr Glu Leu Leu Glu Glu Asp Asp
    275                 280                 285 cgc gat gag aac tcc agc cac gac ttt ggc aaa gat ttg att ccc aag      912
Arg Asp Glu Asn Ser Ser His Asp Phe Gly Lys Asp Leu Ile Pro Lys
290                 295                 300 atc acc gaa gcc ggt ctg gcc tat gcg cac ccg ttc ccg ctc tct tgc      960
Ile Thr Glu Ala Gly Leu Ala Tyr Ala His Pro Phe Pro Leu Ser Cys
305                 310                 315                 320 gta caa tcc gac ccg gat gcc gag ccg tac tgg cgc gat gtg ggt acg     1008
Val Gln Ser Asp Pro Asp Ala Glu Pro Tyr Trp Arg Asp Val Gly Thr
            325                 330                 335 ctg gaa gct tac tgg aaa gcg aac ctc gat ctg gcc tct gtg gtg ccg     1056
Leu Glu Ala Tyr Trp Lys Ala Asn Leu Asp Leu Ala Ser Val Val Pro
        340                 345                 350 aaa ctg gat atg tac gat cgc aat tgg cca att cgc acc tac aat gaa     1104
Lys Leu Asp Met Tyr Asp Arg Asn Trp Pro Ile Arg Thr Tyr Asn Glu
    355                 360                 365 tca tta ccg cca gcg aaa ttc gtg cag gat cgc tcc ggt agc cac ggg     1152
Ser Leu Pro Pro Ala Lys Phe Val Gln Asp Arg Ser Gly Ser His Gly
370                 375                 380 atg acc ctt aac tca ctg gtt tcc gac ggt tgt gtg atc tcc ggt tcg     1200
Met Thr Leu Asn Ser Leu Val Ser Asp Gly Cys Val Ile Ser Gly Ser
385                 390                 395                 400 gtg gtg gtg cag tcc gtt ctg ttc tcg cgc gtt cgc gtg aat tca ttc     1248
Val Val Val Gln Ser Val Leu Phe Ser Arg Val Arg Val Asn Ser Phe
            405                 410                 415 tgc aac att gat tcc gcc gta ttg tta ccg gaa gta tgg gta ggt cgc     1296
Cys Asn Ile Asp Ser Ala Val Leu Leu Pro Glu Val Trp Val Gly Arg
        420                 425                 430 tcg tgc cgt ctg cgc cgc tgc gtc atc gat cgt gct tgt gtt att ccg     1344
Ser Cys Arg Leu Arg Arg Cys Val Ile Asp Arg Ala Cys Val Ile Pro
    435                 440                 445 gaa ggc atg gtg att ggt gaa aac gca gag gaa gat gca cgt cgt ttc     1392
Glu Gly Met Val Ile Gly Glu Asn Ala Glu Glu Asp Ala Arg Arg Phe
450                 455                 460 tat cgt tca gaa gaa ggc atc gtg ctg gta acg cgc gaa atg cta cgg     1440
Tyr Arg Ser Glu Glu Gly Ile Val Leu Val Thr Arg Glu Met Leu Arg
465                 470                 475                 480 aag tta ggg cat aaa cag gag cga taa                                 1467
Lys Leu Gly His Lys Gln Glu Arg
```

-continued

```
                        485

<210> SEQ ID NO 2
<211> LENGTH: 488
<212> TYPE: PRT
<213> ORGANISM: Artificial Sequence
<220> FEATURE:
<223> OTHER INFORMATION: Description of Artificial Sequence: Pea ssu TP
      linked to E. coli glgC16 CDS

<400> SEQUENCE: 2

Met Ala Ser Met Ile Ser Ser Ala Val Thr Thr Val Ser Arg Ala
 1               5                  10                  15

Ser Thr Val Gln Ser Ala Ala Val Ala Pro Phe Gly Gly Leu Lys Ser
                20                  25                  30

Met Thr Gly Phe Pro Val Lys Lys Val Asn Thr Asp Ile Thr Ser Ile
            35                  40                  45

Thr Ser Asn Gly Gly Arg Val Lys Cys Met Leu Ser Leu Glu Lys Asn
        50                  55                  60

Asp His Leu Met Leu Ala Arg Gln Leu Pro Leu Lys Ser Val Ala Leu
65                  70                  75                  80

Ile Leu Ala Gly Gly Arg Gly Thr Arg Leu Lys Asp Leu Thr Asn Lys
                85                  90                  95

Arg Ala Lys Pro Ala Val His Phe Gly Gly Lys Phe Arg Ile Ile Asp
                100                 105                 110

Phe Ala Leu Ser Asn Cys Ile Asn Ser Gly Ile Arg Arg Met Gly Val
            115                 120                 125

Ile Thr Gln Tyr Gln Ser His Thr Leu Val Gln His Ile Gln Arg Gly
        130                 135                 140

Trp Ser Phe Phe Asn Glu Glu Met Asn Glu Phe Val Asp Leu Leu Pro
145                 150                 155                 160

Ala Gln Gln Arg Met Lys Gly Glu Asn Trp Tyr Arg Gly Thr Ala Asp
                165                 170                 175

Ala Val Thr Gln Asn Leu Asp Ile Ile Arg Arg Tyr Lys Ala Glu Tyr
            180                 185                 190

Val Val Ile Leu Ala Gly Asp His Ile Tyr Lys Gln Asp Tyr Ser Arg
        195                 200                 205

Met Leu Ile Asp His Val Glu Lys Gly Val Arg Cys Thr Val Val Cys
    210                 215                 220

Met Pro Val Pro Ile Glu Glu Ala Ser Ala Phe Gly Val Met Ala Val
225                 230                 235                 240

Asp Glu Asn Asp Lys Thr Ile Glu Phe Val Glu Lys Pro Ala Asn Pro
                245                 250                 255

Pro Ser Met Pro Asn Asp Pro Ser Lys Ser Leu Ala Ser Met Gly Ile
            260                 265                 270

Tyr Val Phe Asp Ala Asp Tyr Leu Tyr Glu Leu Leu Glu Glu Asp Asp
        275                 280                 285

Arg Asp Glu Asn Ser Ser His Asp Phe Gly Lys Asp Leu Ile Pro Lys
    290                 295                 300

Ile Thr Glu Ala Gly Leu Ala Tyr Ala His Pro Phe Pro Leu Ser Cys
305                 310                 315                 320

Val Gln Ser Asp Pro Asp Ala Glu Pro Tyr Trp Arg Asp Val Gly Thr
                325                 330                 335

Leu Glu Ala Tyr Trp Lys Ala Asn Leu Asp Leu Ala Ser Val Val Pro
            340                 345                 350
```

Lys Leu Asp Met Tyr Asp Arg Asn Trp Pro Ile Arg Thr Tyr Asn Glu
            355                 360                 365

Ser Leu Pro Pro Ala Lys Phe Val Gln Asp Arg Ser Gly Ser His Gly
    370                 375                 380

Met Thr Leu Asn Ser Leu Val Ser Asp Gly Cys Val Ile Ser Gly Ser
385                 390                 395                 400

Val Val Val Gln Ser Val Leu Phe Ser Arg Val Arg Val Asn Ser Phe
                405                 410                 415

Cys Asn Ile Asp Ser Ala Val Leu Leu Pro Glu Val Trp Val Gly Arg
            420                 425                 430

Ser Cys Arg Leu Arg Arg Cys Val Ile Asp Arg Ala Cys Val Ile Pro
        435                 440                 445

Glu Gly Met Val Ile Gly Glu Asn Ala Glu Glu Asp Ala Arg Arg Phe
    450                 455                 460

Tyr Arg Ser Glu Glu Gly Ile Val Leu Val Thr Arg Glu Met Leu Arg
465                 470                 475                 480

Lys Leu Gly His Lys Gln Glu Arg
                485

<210> SEQ ID NO 3
<211> LENGTH: 421
<212> TYPE: DNA
<213> ORGANISM: Triticum aestivum
<220> FEATURE:
<221> NAME/KEY: promoter
<222> LOCATION: (1)..(421)
<223> OTHER INFORMATION: High Molecular Weight Glutenin Promoter Genomic
      DNA

<400> SEQUENCE: 3
cccagctttg agtggccgta gatttgcaaa agcaatggct aacagacaca tattctgcca      60
aaccccaaga aggataatca cttttcttag ataaaaaga acagaccaat atacaaacat     120
ccacacttct gcaaacaata catcagaact aggattacgc cgattacgtg gctttagcag    180
actgtccaaa aatctgtttt gcaaagctcc aattgctcct tgcttatcca gcttcttttg    240
tgttggcaaa ctgcgctttt ccaaccgatt ttgttcttct cgcgctttct tcttagccta    300
aacaaacctc accgtgcacg cagccatggt cctgaacctt cacctcgtcc ctataaaagc    360
ctagccaacc ttcacaatct tatcatcacc cacaacaccg agcaccacaa actagagatc    420
c                                                                    421

<210> SEQ ID NO 4
<211> LENGTH: 43
<212> TYPE: DNA
<213> ORGANISM: Artificial Sequence
<220> FEATURE:
<221> NAME/KEY: primer_bind
<222> LOCATION: (1)..(19)
<223> OTHER INFORMATION: Primer to 3' end of ssu transit peptide
<221> NAME/KEY: primer_bind
<222> LOCATION: (20)..(43)
<223> OTHER INFORMATION: Primer to 5' end of glgA CDS
<223> OTHER INFORMATION: Description of Artificial Sequence: Oligo
      primer

<400> SEQUENCE: 4
tggtggaaga gtaaagtgca tgcaggtttt acatgtatgt tca                       43

<210> SEQ ID NO 5
<211> LENGTH: 54
<212> TYPE: DNA

```
<213> ORGANISM: Artificial Sequence
<220> FEATURE:
<221> NAME/KEY: primer_bind
<222> LOCATION: (1)..(19)
<223> OTHER INFORMATION: Primer to 3' end of glgC CDS
<221> NAME/KEY: primer_bind
<222> LOCATION: (26)..(54)
<223> OTHER INFORMATION: Primer to 3' end of glgA CDS
<223> OTHER INFORMATION: Description of Artificial Sequence: Oligo
      primer

<400> SEQUENCE: 5
tcgctcctgt ttatgccctta gatctctatt tcgagcgata gtaaagctca cggt           54

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Oligo
      primer
<221> NAME/KEY: primer_bind
<222> LOCATION: (11)..(33)
<223> OTHER INFORMATION: Primer to 5' end of ssu transit peptide

<400> SEQUENCE: 6
acgtagatct atggcttcta tgatatcctc ttc                                    33

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Oligo
      primer
<221> NAME/KEY: primer_bind
<222> LOCATION: (10)..(36)
<223> OTHER INFORMATION: Primer to 5' end of HMWG promoter

<400> SEQUENCE: 7
gacatcgatc ccagctttga gtggccgtag atttgc                                 36

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Oligo
      primer
<221> NAME/KEY: primer_bind
<222> LOCATION: (10)..(39)
<223> OTHER INFORMATION: primer to 3' end of HMWG promoter

<400> SEQUENCE: 8
gacgaattcg gatctctagt ttgtggtgct cggtgttgt                              39

<210> SEQ ID NO 9
<211> LENGTH: 32
<212> TYPE: DNA
<213> ORGANISM: Artificial Sequence
<220> FEATURE:
<221> NAME/KEY: primer_bind
<222> LOCATION: (9)..(32)
<223> OTHER INFORMATION: Primer to 5' end of nopaline synthase
      terminator
<223> OTHER INFORMATION: Description of Artificial Sequence: Oligo
      primer

<400> SEQUENCE: 9
caggatccga atttcacccg atcgttcaaa ca                                     32
```

```
<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Oligo
      primer
<221> NAME/KEY: primer_bind
<222> LOCATION: (23)..(50)
<223> OTHER INFORMATION: Primer to 3' end of nopaline synthase
      terminator

<400> SEQUENCE: 10
gacccgcggc tcgaggcggc cgcccgatct agtaacatag atgacaccgc                    50
```